(12) United States Patent
Elia et al.

(10) Patent No.: US 12,016,826 B2
(45) Date of Patent: Jun. 25, 2024

(54) SYSTEMS AND METHODS FOR BIOIMPEDANCE BODY COMPOSITION MEASUREMENT

(71) Applicant: ART MEDICAL Ltd., Netanya (IL)

(72) Inventors: Liron Elia, Kiryat-Ata (IL); Gavriel J. Iddan, Haifa (IL)

(73) Assignee: ART MEDICAL Ltd., Netanya (IL)

( * ) Notice: Subject to any disclaimer, the term of this patent is extended or adjusted under 35 U.S.C. 154(b) by 0 days.

(21) Appl. No.: 17/679,175

(22) Filed: Feb. 24, 2022

(65) Prior Publication Data

US 2022/0175620 A1    Jun. 9, 2022

Related U.S. Application Data

(63) Continuation of application No. 17/094,899, filed on Nov. 11, 2020, now Pat. No. 11,266,575, which is a
(Continued)

(51) Int. Cl.
*A61J 15/00* (2006.01)
*A61B 5/00* (2006.01)
(Continued)

(52) U.S. Cl.
CPC ......... *A61J 15/0084* (2015.05); *A61B 5/0205* (2013.01); *A61B 5/361* (2021.01);
(Continued)

(58) Field of Classification Search
None
See application file for complete search history.

(56) References Cited

U.S. PATENT DOCUMENTS

| 5,513,648 A | 5/1996 | Jackson |
| 2004/0059242 A1* | 3/2004 | Masuo ................. A61B 5/6826 600/547 |

(Continued)

FOREIGN PATENT DOCUMENTS

| AT | 516499 | 6/2016 |
| CA | 3046117 | 6/2018 |

(Continued)

OTHER PUBLICATIONS

English machine translation of CN-1492744-A, Clarivate Analytics, 22 pages, printed on Nov. 28, 2023 (Year: 2023).*
(Continued)

*Primary Examiner* — Matthew Kremer

(57) ABSTRACT

There is provided a system for monitoring a heart of a subject and monitoring impedance-related parameters, comprising: a feeding tube, an electrode disposed(s) on a distal end of the feeding tube, a controller that performs, while the feeding tube is in located in an esophagus and feeding is delivered to a subject via the feeding tube, in a plurality of iterations: continuously measuring voltage at the electrode(s) of the feeding tube, applying alternating current(s) between the electrode(s) of the feeding tube and at least one other electrode, computing impedance measurement(s) from the electrode(s) of the feeding tube according to the applied alternating current(s) and the measured voltage, computing impedance-related parameter(s) based on the impedance measurement(s), terminating the application of the alternating current(s), obtaining an electrocardiogram (ECG) measurement based on the voltage measured at the electrode(s) of the feeding tube, and providing the impedance-related parameter(s) and the ECG measurement.

13 Claims, 21 Drawing Sheets

Related U.S. Application Data continuation-in-part of application No. PCT/IL2019/051210, filed on Nov. 5, 2019.

(60) Provisional application No. 62/755,650, filed on Nov. 5, 2018.

(51) Int. Cl.
| | |
|---|---|
| *A61B 5/0205* | (2006.01) |
| *A61B 5/361* | (2021.01) |
| *A61B 5/363* | (2021.01) |
| *A61M 5/172* | (2006.01) |
| *A61M 16/00* | (2006.01) |
| *A61N 1/362* | (2006.01) |
| *A61N 1/39* | (2006.01) |
| *A61B 5/0537* | (2021.01) |
| *A61B 5/0538* | (2021.01) |
| *A61B 5/08* | (2006.01) |

(52) U.S. Cl.
CPC ............ *A61B 5/363* (2021.01); *A61B 5/6852* (2013.01); *A61B 5/687* (2013.01); *A61M 5/1723* (2013.01); *A61M 16/024* (2017.08); *A61N 1/3629* (2017.08); *A61N 1/3956* (2013.01); *A61B 5/0537* (2013.01); *A61B 5/0538* (2013.01); *A61B 5/0809* (2013.01); *A61M 2230/04* (2013.01); *A61M 2230/65* (2013.01)

(56) References Cited

U.S. PATENT DOCUMENTS

| | | | |
|---|---|---|---|
| 2005/0177060 A1 | 8/2005 | Yamazaki et al. | |
| 2007/0161894 A1* | 7/2007 | Zdeblick | A61B 5/053 600/437 |
| 2008/0076970 A1 | 3/2008 | Foulis et al. | |
| 2008/0249507 A1 | 10/2008 | Hadani | |
| 2008/0306401 A1 | 12/2008 | Okura | |
| 2010/0076328 A1 | 3/2010 | Matsumura et al. | |
| 2011/0144481 A1 | 6/2011 | Feer et al. | |
| 2013/0012790 A1* | 1/2013 | Horseman | A61B 5/6891 600/301 |
| 2016/0150994 A1* | 6/2016 | Smith | A61B 5/7221 600/547 |
| 2016/0331273 A1 | 11/2016 | Armoundas | |
| 2016/0367196 A1 | 12/2016 | Kim et al. | |
| 2017/0042615 A1* | 2/2017 | Salahieh | A61B 1/00179 |
| 2018/0071532 A1* | 3/2018 | Carter | A61N 1/36036 |
| 2018/0078195 A1* | 3/2018 | Sutaria | A61B 5/1073 |
| 2019/0083725 A1 | 3/2019 | Elia et al. | |
| 2019/0313970 A1 | 10/2019 | Elia et al. | |
| 2021/0059905 A1 | 3/2021 | Elia et al. | |

FOREIGN PATENT DOCUMENTS

| | | | | |
|---|---|---|---|---|
| CN | 1492744 A | * | 4/2004 | ........... A61B 5/0537 |
| CN | 101754717 | | 6/2010 | |
| CN | 106456042 | | 2/2017 | |
| CN | 107949328 | | 4/2018 | |
| DE | 10023141 | | 11/2001 | |
| GB | 2530355 A | * | 3/2016 | ........... A61B 5/0536 |
| JP | 4124649 | | 5/2008 | |
| JP | 2009-5904 | | 1/2009 | |
| JP | 2010-227408 | | 10/2010 | |
| JP | 2013-202104 | | 10/2013 | |
| JP | 2016-511032 | | 4/2016 | |
| JP | 2017-116415 | | 6/2017 | |
| WO | WO 2006/060458 | | 6/2006 | |
| WO | WO 2011/075767 | | 6/2011 | |
| WO | WO-2012158748 A1 | * | 11/2012 | ........... A61B 5/0002 |
| WO | WO 2018/185738 | | 10/2018 | |
| WO | WO 2020/095298 | | 5/2020 | |
| WO | WO 2022/101897 | | 5/2022 | |

OTHER PUBLICATIONS

Final Official Action dated May 19, 2021 from the US Patent and Trademark Office Re. U.S. Appl. No. 17/094,899. (11 pages).
International Preliminary Report on Patentability dated May 20, 2021 From the International Bureau of WIPO Re. Application No. PCT/IL2019/051210. (12 Pages).
International Search Report and the Written Opinion dated Jul. 13, 2020 From the International Searching Authority Re. Application No. PCT/IL2019/051210. (18 Pages).
Invitation to Pay Additional Fees, Communciation Relating to the Results of the Partial International Search and the Provisional Opinion dated Feb. 18, 2020 From the International Searching Authority Re. Application No. PCT/IL2019/051210. (14 Pages).
Notice of Allowance dated Nov. 1, 2021 from US Patent and Trademark Office Re. U.S. Appl. No. 17/094,899. (6 pages).
Official Action dated Jan. 8, 2021 from the US Patent and Trademark Office Re. U.S. Appl. No. 17/094,899. (13 pages).
Bera et al. "Switching of the Surface Electrode Array in A 16-Electrode EIT System Using 8-Bit Parallel Digital Data", 2011 World Congress on Information and Communication Technologies, WICT, XP032104144, Mumbai, India, Dec. 11-14, 2011, p. 1288-1293, Dec. 11, 2011.
Bera et al. "Switching of the Surface Electrode Array in A 16-Electrode EIT System Using 8-Bit Parallel Digital Data", Proceedings of the IEEE 2011 World Congress on Information and Communication Technologies, WICT'11, Mumbai, India, Dec. 11-14, 2011, XP032104144, p. 1288-1293, Dec. 11, 2011.
Examination Report Under Sections 12 & 13 of the Patents Act, 1970 and the Patents Rules, 2003 dated Jan. 23, 2023 From the Government of India, Intellectual Property India, Patents, Designs, Trade Marks, Geographical Indications, The Patent Office Re. Application No. 202127022583. (6 pages).
International Preliminary Report on Patentability dated May 25, 2023 From the International Bureau of WIPO Re. Application No. PCT IL2021/051319. (14 Pages).
Notice of Reason(s) for Rejection dated Sep. 26, 2023 From the Japan Patent Office Re. Application No. 2021-523419 and Its Translation Into English. (12 Pages).
Communication Pursuant to Article 94(3) EPC Dated Mar. 11, 2024 From the European Patent Office Re. Application No. 19805765.5 (5 Pages).
English Summary Dated Jan. 19, 2024 Notification of Office Action Dated Jan. 4, 2024 From the National Intellectual Property Administration of the People's Republic of China Re. Application No. 201980077821.6. (12 Pages).
Machine Translation Dated Jan. 15, 2024 of Notification of Office Action and Search Report Dated Jan. 4, 2024 From the National Intellectual Property Administration of the People's Republic of China Re. Application No. 201980077821.6. (18 Pages).
Notification of Office Action and Search Report Dated Jan. 4, 2024 From the National Intellectual Property Administration of the People's Republic of China Re. Application No. 201980077821.6. (17 Pages).

\* cited by examiner

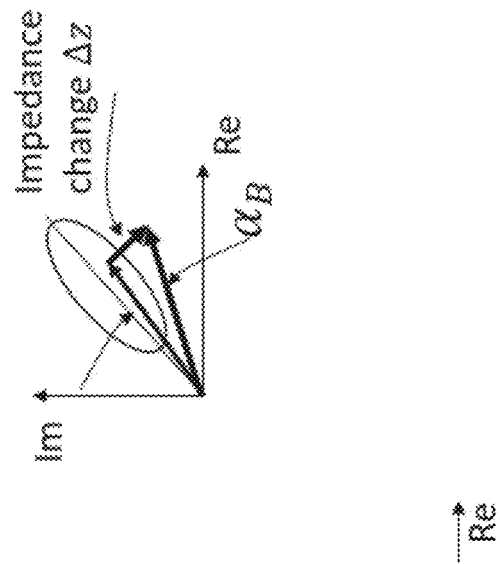
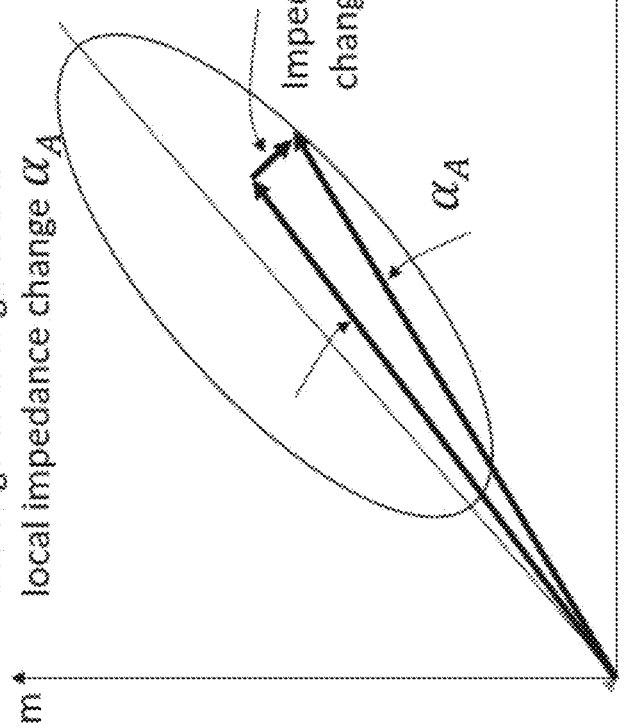
FIG. 12

BIS EQUATIONS calculation FLOW procedure

1. Read sensor data [Ω] :
   1.1 $R_0$ (also known as $R_E$)
   1.2 $R_{50k}$
   1.3 $X_{50k}$
   1.4 $R_\infty$ 2. Patient personal data :
   2.1 W [Kg]
   2.2 H [cm]
   2.3 F=1 M=0

3. Constants:
   3.1 $k_E(F) = 0.3$      $k_E(M) = 0.307$
   3.2 $\varrho_E(F) = 39\ [\Omega\ cm]$    $\varrho_E(M) = 40.5\ [\Omega\ cm]$
   3.3 $\varrho_I(F) = 264.9\ [\Omega\ cm]$    $\varrho_I(M) = 273.9\ [\Omega\ cm]$
   3.4 $K_B = 4.3$
   3.5 $D = 1.05\ [gr/ml]$

FIG. 14

4. calculations:

4.1 $ECW = k_E \left( \dfrac{H^2 \cdot \sqrt{W}}{R_E} \right)^{2/3}$  where: $k_E = 0.01 \left( \dfrac{18.5 \, \rho_E^2}{D} \right)^{1/3}$ 4.2 $TBW = ECW \left( \dfrac{\rho_T}{\rho_E} \cdot \dfrac{R_I + R_E}{R_I} \right)^{2/3}$  where: $\dfrac{\rho_T}{\rho_E} = \dfrac{\rho_I}{\rho_E} - \left( \dfrac{\rho_I}{\rho_E} - 1 \right) \left( \dfrac{R_I}{R_E} \right)^{2/3}$ 4.3 $ICW = TBW - ECW$ [Kg]

4.4 $FFM = 1.11 \cdot ECW + 1.52 \cdot ICW$ [Kg]

4.5 $\%FM = \dfrac{W - FFM}{W}$

FIG. 15

SYSTEMS AND METHODS FOR BIOIMPEDANCE BODY COMPOSITION MEASUREMENT

RELATED APPLICATIONS

This application is a continuation of U.S. patent application Ser. No. 17/094,899 filed on Nov. 11, 2020, which is a Continuation-in-Part (CIP) of PCT Patent Application No. PCT/IL2019/051210 having International Filing Date of Nov. 5, 2019, which claims the benefit of priority under 35 USC § 119(e) of U.S. Provisional Patent Application No. 62/755,650 filed on Nov. 5, 2018. The contents of the above applications are all incorporated by reference as if fully set forth herein in their entirety.

FIELD AND BACKGROUND OF THE INVENTION

The present invention, in some embodiments thereof, relates to body composition measurement and, more specifically, but not exclusively, to systems and methods for measurement of body composition using impedance measurements.

Body composition measurement is a valuable tool for example, for assessing nutritional status and/or physical fitness in a variety of clinical settings.

The most commonly used methods to assess body composition in vivo are dual-energy X-ray absorptiometry (DXA), computerized tomography (CT), and magnetic resonance imaging (MRI). Although these imaging methods are accurate in measuring body composition, their practical use is limited (e.g., for routine measurements), for example, because of high cost, large amount of time needed to perform measurement (e.g., to acquire MRI images), and radiation exposure in CT and/or DXA. Therefore, bioelectrical impedance measurement, which are low cost, fast, and do not expose the patient to radiation, are increasingly being implemented for monitoring of patients and for nutritional management and control of patients muscle mass and hydration status in the ICU.

SUMMARY OF THE INVENTION

According to a first aspect, a system for monitoring a heart of a subject and monitoring parameters based on impedance measurements of the subject, comprises: a feeding tube for insertion into a distal end of an esophagus of the subject, at least one electrode disposed on a distal end of the feeding tube at a location such that at least one electrode is located at the distal end of the esophagus of the subject when in use, a controller that performs, while the feeding tube is in located in the esophagus and feeding is delivered to the subject via the feeding tube, in a plurality of iterations: continuously measuring voltage at the at least one electrode of the feeding tube, applying at least one alternating current between the at least one electrode of the feeding tube and at least one other electrode, computing at least one impedance measurement from the at least one electrode of the feeding tube according to the applied at least one alternating current and the measured voltage, computing at least one impedance-related parameter based on the at least one impedance measurement, terminating the application of the at least one alternating current, obtaining an electrocardiogram (ECG) measurement based on the voltage measured at the at least one electrode of the feeding tube, and providing the at least one impedance-related parameter and the ECG measurement.

According to a second aspect, a method of monitoring a heart of a subject and monitoring parameters based on impedance measurements of the subject, comprises: providing a feeding tube for insertion into a distal end of an esophagus of the subject, providing at least one electrode disposed on a distal end of the feeding tube at a location such that at least one electrode is located at the distal end of the esophagus of the subject when in use, while the feeding tube is in located in the esophagus and feeding is delivered to the subject via the feeding tube, in a plurality of iterations: continuously measuring voltage at the at least one electrode of the feeding tube, applying at least one alternating current between the at least one electrode of the feeding tube and at least one other electrode, computing at least one impedance measurement from the at least one electrode of the feeding tube according to the applied at least one alternating current and the measured voltage, computing at least one impedance-related parameter based on the at least one impedance measurement, terminating the application of the at least one alternating current, obtaining an electrocardiogram (ECG) measurement based on the voltage measured at the at least one electrode of the feeding tube, and providing the at least one impedance-related parameter and the ECG measurement.

According to a third aspect, a computer program product for monitoring a heart of a subject and monitoring parameters based on impedance measurements of the subject, comprises program instructions which, when executed by a processor, cause the processor to perform, while a feeding tube is in located in a distal end of an esophagus of the subject and feeding is delivered to the subject via the feeding tube, in a plurality of iterations: continuously measuring voltage by at least one electrode of disposed on a distal end of the feeding tube at a location such that at least one electrode is located at the distal end of the esophagus of the subject when in use, applying at least one alternating current between the at least one electrode of the feeding tube and at least one other electrode, computing at least one impedance measurement from the at least one electrode of the feeding tube according to the applied at least one alternating current and the measured voltage, computing at least one impedance-related parameter based on the at least one impedance measurement, terminating the application of the at least one alternating current, obtaining an electrocardiogram (ECG) measurement based on the voltage measured at the at least one electrode of the feeding tube, and providing the at least one impedance-related parameter and the ECG measurement.

In a further implementation form of the first, and second aspects, the controller further performs: analyzing the ECG measurement to determine an indication of cardiac abnormality, and applying via the at least one electrode of the feeding tube, an electrical pattern selected for treating the cardiac abnormality.

In a further implementation form of the first, and second aspects, the at least one electrode of the feeding tube comprises a plurality of electrodes, and analyzing comprises analyzing each respective ECG measurement by each respective ECG electrode, and wherein the controller further performs: selecting a respective electrical pattern based on the analysis of each respective ECG measurement, and applying by each of the plurality of electrodes of the feeding tube, the respective electrical pattern for treating the cardiac abnormality.

In a further implementation form of the first, and second aspects, the electrical pattern is selected from the group consisting of: defibrillation electrical pattern for treating the cardiac abnormality of ventricular fibrillation (VF) and/or ventricular tachycardia (VT), cardiac pacing electrical pattern for treating the cardiac abnormality of abnormal heart rate and/or block in electrical conduction in the heart, and cardioversion electrical pattern for treating the cardiac abnormality of cardiac arrhythmia convertible to normal sinus rhythm.

In a further implementation form of the first, and second aspects, the electrical pattern applied via the at least one electrode of the feeding tube has significantly less power in comparison to an electrical pattern applied via extracorporeal electrodes to a skin surface of a chest of the subject.

In a further implementation form of the first, and second aspects, the electrical pattern applied via the at least one electrode of the feeding tube has a power of less than about 50 Joules when the electrical pattern applied via extracorporeal electrodes is about 100 to 500 Joules.

In a further implementation form of the first, and second aspects, the analyzing the ECG measurements to determine the indication of cardiac abnormality and the application of the electrical pattern are iterated in the plurality of iterations.

In a further implementation form of the first, and second aspects, the controller further performs: in response to the determined indication of cardiac abnormality, generating instructions for execution by a feeding controller for halting the feeding of the subject via the feeding tube, and in response to the execution by the feeding controller for halting of the feeding, performing the application of the electrical pattern.

In a further implementation form of the first, and second aspects, the at least one impedance-related parameter comprises a body composition of a body segment located between the at least one electrode of the feeding tube and the at least one other electrode located externally to a body of the subject, wherein the controller further performs: analyzing a combination of the ECG measurement and the at body composition to determine likelihood of a certain cardiac abnormality selected from a plurality of cardiac abnormalities, and applying via the at least one electrode of the feeding tube, an electrical pattern selected to treat the certain cardiac abnormality.

In a further implementation form of the first, and second aspects, the body composition comprises lung fluid and the body segment comprises a lung.

In a further implementation form of the first, and second aspects, the analyzing the ECG measurements to determine the indication of cardiac abnormality and the application of the electrical pattern are iterated in the plurality of iterations.

In a further implementation form of the first, and second aspects, the at least one impedance-related parameter comprises at least one breathing parameter indicative of respiration effort of the subject, wherein the controller further performs: analyzing a combination of the ECG measurement and the at least one breathing parameter to determine likelihood of a combined cardiac abnormality and respiratory abnormality, and at least one of: (i) applying via the at least one electrode of the feeding tube, an electrical pattern selected to treat the certain cardiac abnormality, and (ii) generating instructions for execution by a mechanical ventilator that mechanically ventilates the subject, for adjustment of a mechanical ventilation pattern applied to the subject for treating the respiratory abnormality.

In a further implementation form of the first, and second aspects, the controller further: generates instructions for adapting at least one of: a feeding and a medication by a feeding controller delivered via the feeding tube according to the ECG measurement.

In a further implementation form of the first, and second aspects, the controller further: analyzes the at least one impedance-related parameter to detect an indication of gastric reflux in the esophagus occurring during a time interval, analyzes the ECG measurement to detect likelihood of no new cardiac abnormality developed during the time interval, and generate an indication that differentiates between gastric reflux and cardiac abnormality.

In a further implementation form of the first, and second aspects, the at least one electrode comprises a plurality of spaced apart electrodes located on the distal end portion of the feeding tube, wherein obtaining comprises obtaining a plurality of ECG measurements, each respective ECG measurement obtained a respective electrode of the plurality of electrodes, wherein each respective ECG measurement denotes a different orientation relative to a heart of the subject according to the respective location of the respective electrode on the feeding tube, wherein the controller further performs: analyzing the plurality of ECG measurements from the plurality of spaced apart electrodes located on the distal end portion of the feeding tube to determine an indication of cardiac abnormality, and applying via the plurality of electrodes of the feeding tube, a selected electrical pattern to treat the cardiac abnormality.

In a further implementation form of the first, and second aspects, the controller further performs: analyzing the at least one impedance-related parameter of the at least one electrode to identify that the at least one electrode is in contact with the lower esophageal sphincter (LES) of the subject, wherein the analyzing is performed during the plurality of iterations for confirming continuous contact between the at least one electrode and the LES during the measurements of the ECG.

In a further implementation form of the first, and second aspects, the at least one electrode comprises a plurality of spaced apart electrodes location on the feeding tubes, the position of the plurality of spaced apart electrodes selected to obtain ECG measurements at a plurality of target orientations relative to the heart when a certain electrode is in contact with the LES.

In a further implementation form of the first, and second aspects, the at least one other electrodes comprises at least one extracorporeal electrode located externally of a body of the subject for contacting the body of the subject.

In a further implementation form of the first, and second aspects, the at least one electrode disposed on the distal end of the feeding tube comprises a plurality of electrodes disposed on the distal end of the feeding tube, wherein the at least one electrode comprises a first electrode of the feeding tube and the at least one other electrode comprises a second electrode of the feeding tube.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 14 includes some exemplary BIS equations, in accordance with some embodiments of the present invention;

FIG. 15 includes some exemplary equations for computing exemplary health parameters, in accordance with some embodiments of the present invention;

DESCRIPTION OF SPECIFIC EMBODIMENTS OF THE INVENTION

Figure 1:
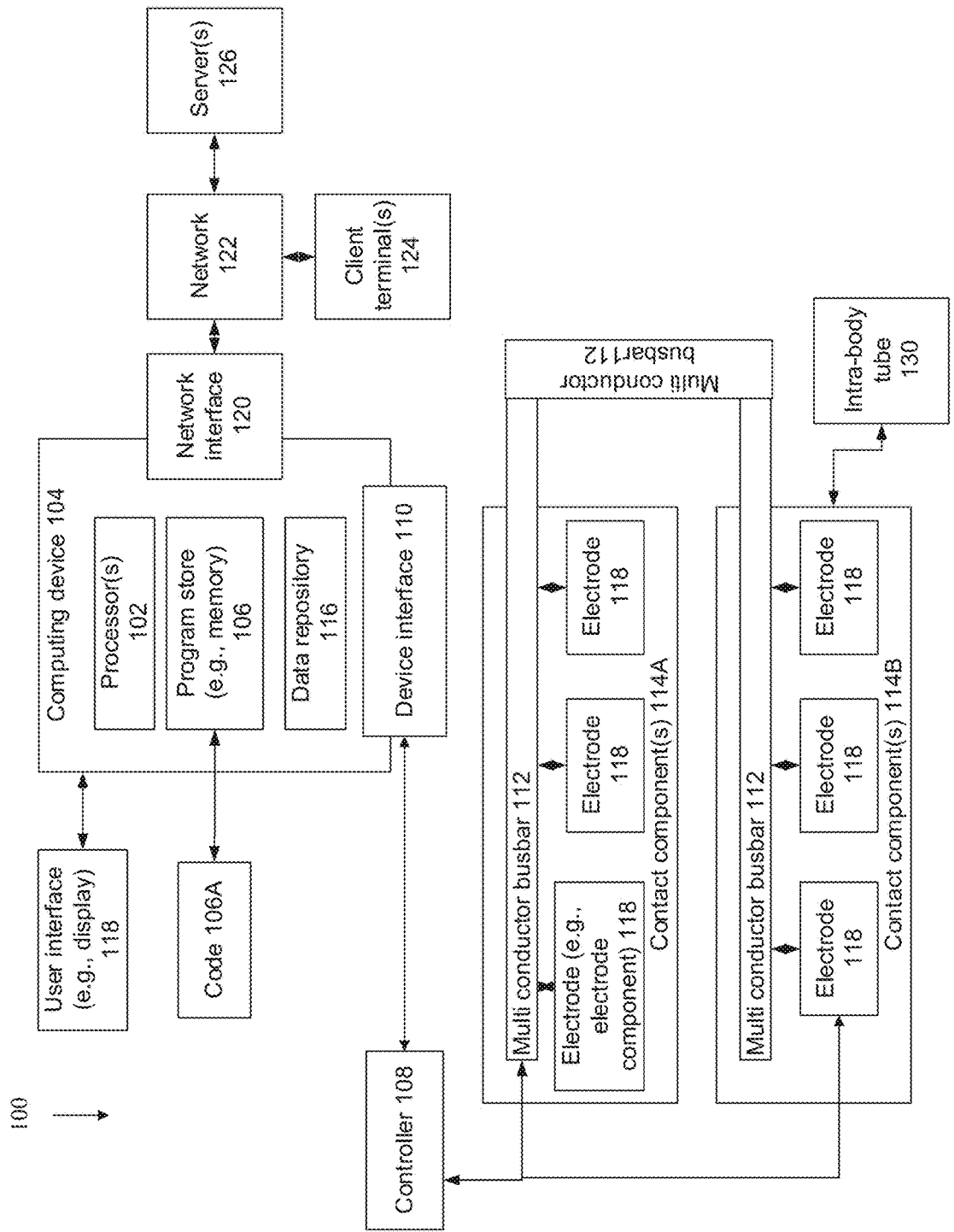
FIG. 1 is a schematic of a system for measuring body composition in one or more body portions of a patient by selectively activating electrodes of a certain contact component of multiple contact components connected by a multi conductor busbar, in accordance with some embodiments of the present invention.

The present invention, in some embodiments thereof, relates to body composition measurement and, more specifically, but not exclusively, to systems and methods for measurement of body composition using impedance measurements.

An aspect of some embodiments of the present invention relates to systems, methods, an apparatus, and/or code instructions (e.g., stored on a memory and executable by hardware processor(s)) for obtaining impedance measurements in one or more body segments of a patient, for example, for estimating and/or measuring and/or bed side monitoring body composition of the respective body segment clinical studies have shown that impedance date and other sensory data of patient body parts, form a clear indication of muscle mass, electrolyte concentrations, and hydration status.

The said information can close loop control the nutritional intake assigned to the treated patient leading to optimal convalescence. The patient may be diagnosed, treatment may be planned, and/or the patient may be treated based on the body composition. Contact component are provided. The contact components, which are designed for placement on the patient, optionally on the skin and inside the patient body include multiple electrodes for contacting the body of the patient. The contact components are separate structures that are not necessarily connected to each other, apart from a multi conductor busbar which connects two or more contact components to a controller. Each contact component may be independently positioned at different locations on the body of the patient and inside the patient. The busbar is flexible, designed to provide freedom of motion for each contact component so that the contact components are positionable at spaced apart locations for monitoring of different body segments. Each contact component and/or each electrode of each contact component is associated with a unique address and includes the corresponding circuits. The controller issues instructions for operation of the electrodes (e.g., as current injectors, current receivers, anodes, cathodes, and/or voltage sensors) over a busbar connected to multiple contact components (at least two), via a respective unique address of the respective contact component and/or busbar (e.g., via an address decoder circuit). The controller issues instructions for operating a selected pair of contact components connected by a common multi conductor busbar using the respective unique address, obtains one or more impedance measurements indicative of impedance of a body segment located between the pair of contact components, and provides the impedance measurement for estimation of body composition of the body segment. The controller may sequentially and/or iteratively activate different pairs of contact components for current injection and other electrodes for impedance measuring of body segments, for example, for real time monitoring. The method enables for the examined body part to have two current injecting electrodes and between them two voltage sensing electrodes which is the desired 4 electrodes approach to impedance sensing yet the two electrodes approach is another embodiment (i.e., pair used for current delivery as well as voltage sensing).

Optionally, each respective contact component includes three electrodes arranged along a long axis of the respective contact component. The controller operates a middle electrode of each contact component of the pair for injecting the current, and as said operates an inner facing electrode of each contact component of the pair for voltage measurement.

As used herein the term inner facing electrode refers to the electrodes of the pair of contact components that are closest to one another. For example, for a pair of contact components placed on the ankle and chest, the inner facing electrode of the ankle contact component is the electrode closest to the chest, and the inner facing electrode of the chest contact component is electrode closest to the ankle (e.g., as depicted by the figures described below).

An aspect of some embodiments of the systems, methods, apparatus, and/or code instructions described herein use the same electrode(s) located on a feeding tube placed within the esophagus of a subject, optionally while feeding is being delivered by the feeding tube, to alternatively and iteratively measure impedance and obtain ECG measurements. Voltage is continuously sensed at the electrode(s) of the feeding tube. An alternating current is applied between the electrode at the feeding tube, and another electrode (also located on the feeding tube and/or an extracorporeal electrode and/or at another location in the body). Impedance is measured using the applied current and voltage. The impedance may be used for computing different parameter for multiple applications as described herein, for example for computing: body composition measurement, amount of lung fluid, breathing parameters, reflux, and location of the feeding tube. When application of current is stopped, ECG is measured based on the voltage sensed at the electrode(s) of the feeding tube. The ECG may be analyzed to determine a cardiac condition, for example, arrhythmia. A suitable electrical pattern may be applied by the same electrode(s) on the feeding tube (and/or other electrodes on the feeding tube) to treat the cardiac condition identified based on the ECG measured at the electrode(s) on the feeding tube, for example, defibrillation, cardiac pacing, and/or cardioversion. The alternating sensing of impedance and ECG, and optionally the treatment, may be continuously iterated for continuous monitoring and/or treatment of the tube fed patient.

At least some implementations of the systems, methods, apparatus, and/or code instructions described herein address the technical problem and/or medical problem and/or improve the technical field, of automatically continuously monitoring and/or treating subjects that are fed using a feeding tube, including monitoring ECG measurements and/or impedance measurements of the subject while the subject is being fed and/or drugs administered using the feeding tube and injections. The technical problem and/or medical problem may further relate to treating the subject based on the ECG measurements while the subject is being fed using the feeding tube. For example, for patient continuous monitoring in the ICU and/or other departments, multiple devices and their associated cabling and/or tubing connecting the patient to monitoring consoles, processors and fluid and vacuum delivery devices are used, which requires a large amount of effort to set up and monitor, and/or increased risk of error and/or unsafe treatment. to be minimized for the sake of improving the patient environment and creating a safer and more convenient surrounding.

At least some implementations of the systems, methods, apparatus, and/or code instructions described herein improve the technical field and/or address the above mentioned technical problem, by a feeding tube with one or more electrodes, and a controller that iteratively terminates any electrical current applied via the electrodes for measuring ECG, and activates the electrodes on the feeding tube and/or drug delivery device for applying an electrical pattern for treating a cardiac condition of the patient based on the measured ECG and/or for applying an electrical current to the at least one electrode on the feeding tube for measuring impedance, for example, for detecting reflux and/or biocomposition of a body segment (e.g., lung fluid and/or other measurements, as described herein). This may reduce the amount of equipment required, increase accuracy of the measurements, increase effectiveness of treatment, and/or reduce risk of error.

At least some implementations of the systems, methods, apparatus, and/or code instructions described herein improve over existing approaches for measuring ECG and/or treating the patients with electrical patterns based on the ECG.

For example, in one approach, electrodes on a tube located in the esophagus are designed for passively measuring ECG, and are unable to apply electrical current for treating the ECG and/or for measuring impedance. In another approach, electrodes on a tube in the esophagus are designed for applying an electrical pattern to treat a cardiac condition of the patient, based on ECG signals measured outside the body of the patient using standard ECG electrodes positioned at standard ECG locations on the skin of the chest of the patient. Different electrodes are used for ECG sensing and for applying the electrical current for treating the heart.

In contrast, at least some implementations of the systems, methods, apparatus, and/or code instructions described herein use the same electrodes on the feeding tube for sensing ECG and for applying an electrical pattern for treating a cardiac condition detected based on the ECG (measured from the same electrodes from which the treatment is applied) and/or for applying an electrical current for measuring one or more impedance-related parameters (e.g., reflux, lung fluid, body composition, breathing parameters). This may enable reducing the amount of electrodes applied to the patient, for example, external standard ECG electrode may not necessarily be required. The amount of devices applied to the patient may be reduced, for example, different devices to measure ECG, reflux, breathing, lung fluid, and/or other body composition. Using a single set of electrodes on the feeding tube, while the patient is being fed, rather than other electrodes and/or devices and/or rather than manual intervention, reduces risk of error, for example, due to incorrectly placed devices, missed manual measurements, and/or incorrectly interpreted measurements. When the single set of electrodes on the feeding tube is used in combination with other devices and/or external electrodes, the accuracy of the measurements and/or effectiveness of the treatment may be improved.

Improved electrical treatment may be delivered to treat cardiac problems of the patient, for example, by combining the ECG data with impedance measurements obtained by the same electrodes, for example, a heart problem that is causing a buildup of fluid in the lungs may be better treated. In another example, feeding of the patient may be stopped and/or adjusted (e.g., reduced rate, different formula) based on the cardiac condition of the patient obtained from the ECG data. In yet another example, a patient medication condition (e.g., chest pain) may be determined to be due to reflux rather than to a heart attack by analyzing the impedance measurement to determine whether reflux is present and/or analyzing ECG data to determine whether the patient is experiencing a heart attack. In yet another example, a mechanical ventilator is adjusted based on a combination of breathing parameters obtained from impedance readings of the electrodes and ECG data obtained from the electrode. All of the previously mentioned examples are using the same set of electrodes on the feeding tube, while the patient is being fed. In yet another example, the amount of energy delivered by the electrodes on the feeding tube to treat cardiac abnormalities (e.g., pacing, defibrillation, inversion) may be significantly lower than the energy that would otherwise be delivered using standard approaches, by extracorporeal electrodes applied to the surface of the chest of the patient from outside the body of the patient. For example, less than 50 Joules by the electrodes located on the feeding tube in comparison to about 200-500, or 160-360, or 100-500 Joules of energy by extracorporeal electrodes. The lower energy may be safer for the patient. Moreover, using the existing electrodes on the feeding tube to apply electrical patterns to treat cardiac conditions determined based on the ECG signals of the same electrodes reduces time from diagnosis to treatment, since the electrical treatment may be provided within a short amount of time (e.g., less than a second, 1-5 seconds) from detection of the cardiac condition. In contrast, using existing approaches, a large amount of time may pass from when the abnormal ECG is identified to when external electrodes are placed on the chest of the patient (since such electrodes are not placed before a problem is actually encountered) and electrical treatment is applied.

Optionally, some embodiments relate to using the skin mounted electrodes for muscle nerve stimulation, optionally by passing low voltage current through muscles (e.g., which may be sore) and/or nerves to enhance their recuperation.

At least some implementations of the systems, methods, apparatus, and/or code instructions described herein relate to the technical problem of reducing a number of cables and/or conductors for measuring impedance of different body segments. At least some implementations of the systems, methods, apparatus, and/or code instructions described herein address the technical problem by the architecture of the contact components with three electrodes thereon located along a long axis of the contact component, and the controller that operates the middle electrode as a current injector and/or current collector, and operates the inner facing electrodes as voltage sensors. A certain contact component may be used to measure impedance of two neighboring segments, for example, for a contact component placed on the trunk of the body, the middle electrode is operated for current, and the end electrode facing the legs is operated for sensing voltage of the leg segment, and the electrode on the other end facing the head is operated for sensing voltage of an upper body segment.

The architecture of the contact component (which includes the triad electrode arrangement along a line for applying current and measuring voltage of the applied current) enables monitoring impedance of body segment(s) located in one direction of the contact component, and to other body segment(s) located in an opposite direction of the same contact component by a small number of conductors. For example, for a contact component positioned on the hip, for body segments from the hip towards the ankle, and other body segments from the hip towards the head. 3 electrodes of the contact component connected to a common busbar may be used instead of 4 independent electrodes each connected to its own pair of cables using standard processes.

The architecture described herein enables positioning the contact components (i.e., electrodes thereon) anywhere on the body of the patient. A small number of conductors on busbars (e.g., one, two, or more) connect the multiple contact components, enabling monitoring of body segments between any selected pair of contact components by addressing hence, avoiding the need for individual conductor(s) per sensor or electrode.

At least some implementations of the systems, methods, apparatus, and/or code instructions described herein relate to the technical problem of improving measurement of impedance of body segments of a patient. At least some implementations of the systems, methods, apparatus, and/or code instructions described herein address the technical problem by the architecture of the contact components with three electrodes thereon located along a long axis of the contact component, and the controller that operates the middle electrode as a current injector and/or current collector, and operates the inner facing electrodes as voltage sensors. Since the current passes between the middle electrodes of the pair of contact components, the voltage measured by the inner electrodes of the pair of contact components more accurately measures the voltage drop resulting from the current itself as the current travels past the inner electrodes on its way to, or coming out from the middle electrodes.

At least some implementations of the systems, methods, apparatus, and/or code instructions described herein relate to the technical problem of improving accuracy of bioelectrical impedance measurements of body parts of a patient. For example, for monitoring patients, such as patients in the intensive care unit (ICU), which may be at risk of, for example, internal bleeding and/or edema. Such patients may be monitored using bioelectrical impedance measurement, which is fast becoming an accepted indication of health status, for example, to detect current body composition, monitor trends of body composition (e.g., getting worse or better), and/or predict future body composition. Each of the triad 3 elements includes a decoder, switches electrodes and amplifier, the last one is activated when the specific electrode is assigned as a voltage sensing electrode. The added amplifier will enable the use of lower injected current which is always clinically desired, without sacrificing good S/N.

Bioelectrical impedance analysis for measurement of body composition (e.g., in the ICU) may be performed using bioelectrical impedance vector analysis (BIVA). For example, repeated BIVA hydration measurements may detect fluid accumulation or fluid balance of >2 liters in ICU patients. Fat-free mass loss (e.g., in patients in the ICU) relates to a worse prognosis for patients with chronic diseases. The association between fat-free mass at intensive care unit admission and 28-day mortality is one indicator. In the ICU population, known to have rapid fluid shifts, phase angle may be predictive of 28-day mortality. The collected sensorial data will enable a closed loop optimal control of patient nutritional intake which has been shown in patient faster convalescence.

At least some implementations of the systems, methods, apparatus, and/or code instructions described herein improve the technology of bioelectrical impedance analysis for measurement of body composition of body part(s) of a patient. The improvement arises, at least in part, from selection of certain electrodes on corresponding contact components (which may include an arrangement of three electrodes spaced apart and along a long axis), which provides measurements of impedance of corresponding body portion(s). Electrodes may be selected according to their respective addresses. A relatively small number of conductors may be used when the segment of each body section is selected by the addressable electrodes. The conductors (metallic layer or carbon based layer such as Graphene and/or inert metals such as gold and the like) may be mounted or deposited on a strip of flexible strip made of thin PCB material and/or Kapton (by Dupont) as an alternative a multiconductor cable can be used. In contrast, existing systems and methods use one conductor for each electrode (for a point measurement at a certain location), which results in complexity of wiring, impractical to measure impedance beyond a small number of locations due to the large number of conducting wires required, and/or interference between signals arising from interference created by the large number of conducing wires.

Although fat-free mass (FFM) contains virtually all the water and conducting electrolytes in the body and FFM hydration is constant, the fundamental assumptions on which other systems and methods are based, is that the body (i.e., limbs and trunk) are considered as a single conductive cylinder and the relationship between the main cross sectional areas remains the same. This assumption is not relevant, for example, for the elderly population, since with aging, the decrease in FFM and a redistribution of adipose tissue from the limbs to the trunk give rise to narrower diameters for the conductive volumes (cylinders) of the limbs. To achieve improved accuracy and sensitivity in bio-impedance body composition measurement each cylinder (i.e., body part, for example, limbs and/or trunk) are measured independently (e.g., segmental measurement) by at least some implementations of the systems, methods, apparatus, and/or code instructions described herein. The body segments reconstruction may include for an easier GUI color coding, for example, blue for high water level and other color such as red for dehydrated body section.

At least some implementations of the systems, methods, apparatus, and/or code instructions described herein improve the process of treating a patient based on bioelectrical impedance measurements. Water and/or electrolyte content of body tissue are of clinical significance when taking care of a patient and/or planning treatment of the patient. They indicative of, for example, dehydration, fat content, edema and other pathological status indicators. Fat, cell boundaries and water electrolyte directly affect the electrical impedance of examined tissue. Hence the measurement of electrical conductance is increasingly being used as an indication of patient health parameters. The improvement provided is at least based on the ability to monitoring multiple different body parameters of the patient, using relatively few conductors. The monitored data may be presented (e.g., in a GUI), analyzed for an indication of an alert, and/or used to predict future clinical states of the patient and closed loop control of patient's nutrition.

At least some implementations of the systems, methods, apparatus, and/or code instructions described herein may improve the technology of performing impedance measurement using a segmental approach. The segmental approach may refer to each impedance measurement being performed on a portion of the body, for example, a leg having a certain impedance (denoted z) rather than the whole-body impedance (denoted Z). It is noted that using the segmental approach, a small change in the impedance $\Delta z$ is be much easier to sense since:

$$\frac{\Delta z}{z} \gg \frac{\Delta z}{Z}$$

Using standard approaches, segmental measurements require a large number of leads and/or cables, which may cause discomfort to the patient, increase complexity, make the system cumbersome, and/or increase risk of error in measurement.

The improvement provided by at least some implementations of the systems, methods, apparatus, and/or code instructions described herein is addressed by performing a segmental impedance measurement approach without the need of a large number of individual conductors and/or individual electrodes as are required by existing systems and methods, and/or the capability of measuring the impedance of interior body organs such as the lungs. The reduction in the number of conductors and/or electrodes is due to the address architecture described herein, where using a small number of conductors—say 5 but less than 10 certain electrodes (e.g., of certain contact components) may be selected, in contrast to existing methods in which each electrode is connected with its own dedicated pair of wires.

At least some implementations of the systems, methods, apparatus, and/or code instructions described herein improve the technology of bioelectrical impedance measurement and/or analysis, by enabling bioelectrical impedance measurement and/or analysis in conditions in which standard impedance measurement processes are inaccurate and/or cannot be used. In some cases, the optimal position for a patient on which impedance measurements are being performed is a full supine position. However, due to clinical constraints the patient may not be placed in the full supine position, for example, in patients with head injury and/or intracranial pressure monitoring, and/or for patients for whom the positioning of the electrodes is modified because of the presence of other devices (e.g., intravenous cannulas and soft restraints). At least some implementations of the systems, methods, apparatus, and/or code instructions described herein enabling positioning electrodes anywhere on the body, and/or the number of electrodes positioned on the body may be large, and/or selection of different electrodes enables performing bioimpedance measurements on any part of the body.

Electrodes, when connected to contact components which are distinct physical structures that are coupled to a common busbar, are positionable anywhere on the body of the patient.

The data thus collected (i.e., impedance measurements of body segments, optionally per body segment as described herein) in conjunction with data from other sensors, for example, respiration, resting energy expenditure, pressure sensor, pulse sensor, sound sensor, and skin conductance sensor, and/or feed rate of nutrients and fluids, for example, as described with reference to international patent application No. IL 2017/051271 by the same inventors as the present application, may be used via artificial intelligence (AI) models in a correlation analysis between muscle mass (i.e., loss and/or gain) and nutrient consumption/delivery/change by the patient in the ICU, with an analysis of the components in the feeding materials. The feeding may be correlated with the data to provide an indication of how the feeding is affecting the muscle status and/or otherwise health status of each body segment, optionally per body segment, since different body segments may experience different rates of muscle mass and/or health changes. For example, muscle mass may increase or decrease proportionally more in peripheral tissue in comparison to central tissue, or vice-versa. Muscle mass and hydration status are considered as an important clinical health and convalescence indicator and hence patient treatment should be tuned towards improving the said muscle mass, the methodology just described will enable it. In comparison, known processes for adapting muscle mass and hydration status are simple manual methods, for example, weighting the patient using a scale, simple blood tests, and/or measuring thigh circumference.

The analysis may be indicative of the effect of body intake and specific food contents on specific body section as analyzed by the impedance (and/or other) body sensors.

Optionally, muscle mass gain and/or loss is monitored (e.g., continuously tracked), optionally per body segment, to allow dynamic food and/or liquids enteral and/or parenteral modification by closed loop optimal control by applying the AI based model correlating the body intake with said muscle mass optionally per body segment. Instructions may be generated, optionally dynamically and/or in real time, for execution by a feeding pump to change the feeding rate and/or food type, to reach a target, for example to adjust the feeding to prevent and/or reverse muscle loss and/or to help the patient gain muscle (e.g., recover from muscle loss). For example, the amount of lipids, carbohydrates, proteins and/or fat in the administered food is controlled according to estimated changes in the muscle mass. The amount of lipids, carbohydrates, proteins and/or fat may be selected based on a correlation dataset that correlates between muscle mass changes and the amount of lipids, carbohydrates, proteins and/or fat which should be administered to patient, for instance with certain physiological parameters, and/or demographic parameters. Different body segments may require different proportions of lipids, carbohydrates, proteins and/or fat, for example, central tissues (e.g., belly) which have a higher proportion of fat may require different proportions of nutrients in comparison to peripheral tissues which may have relatively higher proportion of muscle. The amount may be selected per body segment using the correlation dataset that correlates between muscle mass changes and the amount of lipids, carbohydrates, proteins, and/or fat per body segment. The amount per body segment may be aggregated (e.g., added together, optionally using weights for different body segments) to obtain an overall amount/mixture of nutrition to administer to the patient. The controller may generate instructions for automatic (and/or manual and/or semi-automatic) delivery of the total nutrition (e.g., mix of nutrients and/or amount and/or rate of delivery and/or delivery pattern) to administer to the patient based on the nutrition determined for each segment, for example, by a feeding pump.

The modification may apply to the feed pump rate and/or food specifications, for example, as described with reference to International Patent Application No. IL 2017/051271.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
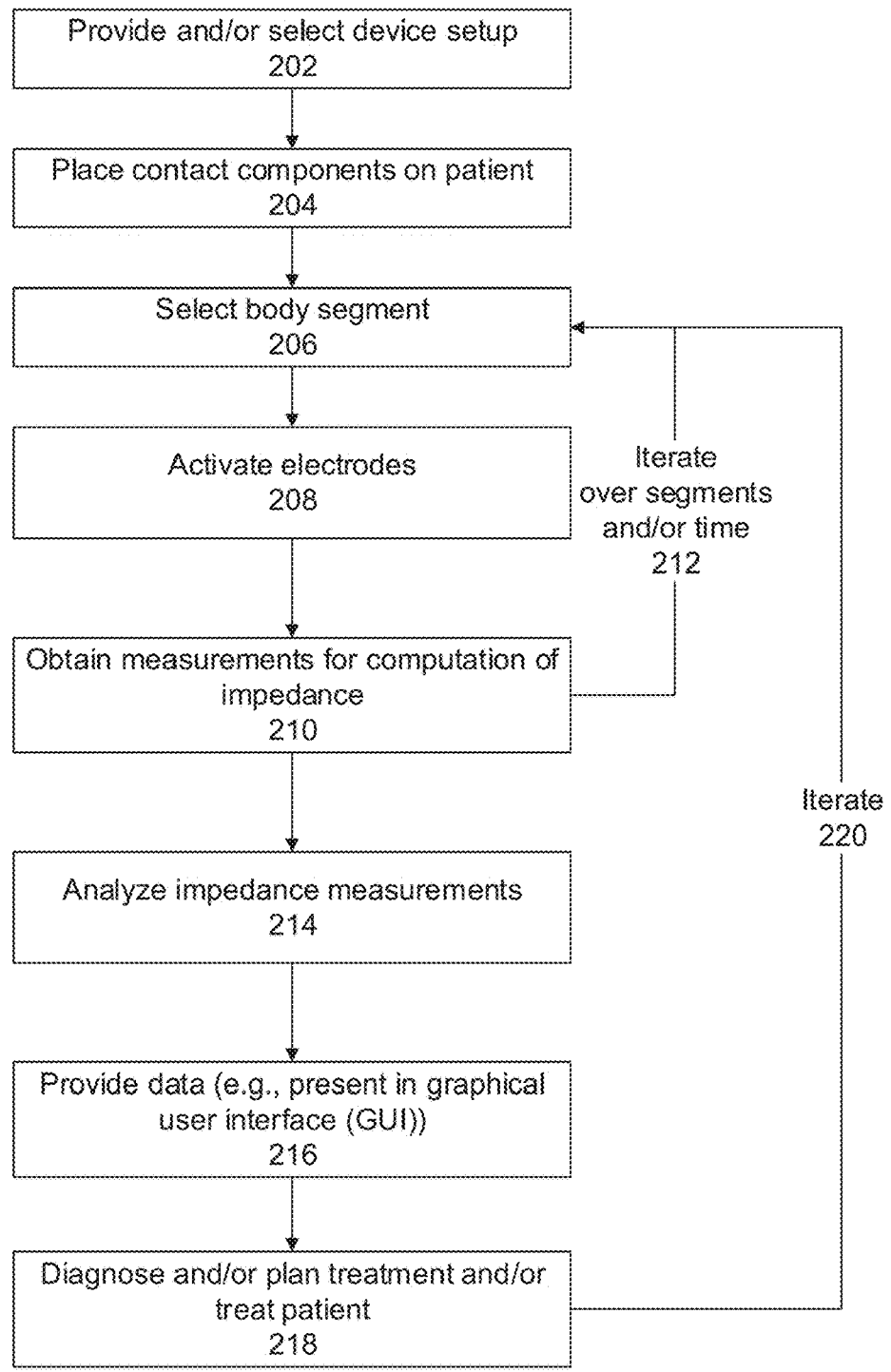
FIG. 2 is a flowchart of a computer implemented method for selectively activating electrodes of a certain contact component of multiple contact components connected by a busbar, in accordance with some embodiments of the present invention.

Reference is now made to FIG. 1, which is a schematic of a system 100 for measuring body composition in one or more body portions of a patient by selectively activating electrodes (e.g., of electrode components) 118 of a certain contact component (e.g., 114A) of multiple contact components (e.g., 114A-B) connected by a multi conductor busbar (also referred to herein as busbar), in accordance with some embodiments of the present invention, by another embodiment other sensors such as pressure, temperature, skin conductivity and pulse piezo sensors may be connected to a busbar in addition to the impedance electrodes and/or as a separate entity. Reference is also made to FIG. 2, which is a flowchart of a computer implemented method for selectively activating electrodes of a certain contact component of multiple contact components connected by a busbar, in accordance with some embodiments of the present invention. Electrodes 118 (optionally within an electrode component including sub-components such as address decoder and/or switches, as described herein) of contact components 114A-B, optionally three per contact component, may be spaced apart and arranged along a long axis (i.e., substantially straight ling) of the respective contact component. One or more acts of the method described with reference to FIG. 2 may be implemented by components of system 100, as described herein, for example, by a processor(s) 102 of a computing device 104 executing code instructions 106A stored in a program store (e.g., memory) 106.

Computing device 104 is in electrical communication with a controller 108 (e.g., combined transmitter and receiver components, or separate transmitter and receiver components 108) that generates instructions for selection of electrodes 118 on a certain contact component (e.g., 114A) from multiple contact components (e.g., 114A-B). Each set of electrodes 118 on each contact component (e.g., 114A-B) are connected to a busbar 112.

As used herein, the term electrodes (e.g., 118) may sometimes be interchanged with the term electrode component, and/or may sometimes refer to the electrode of the electrode component which includes additional sub-components such as address decoder circuitry and/or switches, or other bio sensors as described herein.

Each contact component may be made of, for example, flexible printed circuit board and/or plastic and/or cloth, optionally flexible. Each contact component may include surface for placement against the bod of the patient, optionally against the skin. The surface may include an adhesive.

Optionally, one busbar 112 connects all of the electrodes on all of the contact components. Alternatively, multiple busbars 112 are used, where each busbar 112 connects two or more contact components and coupled electrodes. Each busbar 112 may be implemented, for example, multiple conduction lines (e.g., wires, strips of metal or other good conducting materials), optionally a single wire per dedicated task, for example, a line per each of: current, ground, power, voltage sensing, and/or addressing, as described herein.

It is noted that there are multiple contact components. Two contact components 114A-B are depicted as an example. Each contact component may include the same or different number of electrodes 118 thereon. Optionally, each contact component includes three electrodes 118, optionally spaced apart and arranged along an axis (i.e., substantially straight line).

Controller 108 may include a transceiver for injection of electrical signals to the electrodes assigned by the address code as current electrodes of the selected contact component, and receiving a signal from the electrodes of another contact component assigned by the address code as sensing electrodes, for example, the signal is injected into one electrode of one contact component which acts as a transmitter and a measurement of the received signal by another electrode of another contact component is performed. Computing device 104 generates instructions for operating controller 108, and/or receives data from controller 108, optionally via a device interface 110. Alternatively, computing device 104 and controller 108 are implemented as a single device and/or controller 108 is integrated within computing device 104, for example, as another hardware component and/or as code installed on computing device 104. When computing device 104 and controller 108 are integrated, device interface 110 may be, for example, an internal software interface.

Optionally, each biosensor is associated with a respective unique address. The biosensors are connected to the multi conductor busbar which is connected to at least some electrodes. The controller operates the biosensors and the electrodes by transmitting a certain unique address on the multi conductor busbar, as described herein.

Output from the other biosensor(s) connected to the multi conductor busbar may be combined with the impedance measurement, for presentation and/or analysis.

The address instructions outputted by the controller may define operation of the corresponding electrode as a current carrier or voltage sensor.

Different components may be individually connected to the controller forming mixed connections.

Optionally, a contact component with correspond electrodes is installed on an intra-body tube(s) 130. In another implementation, the contact component is implemented as the intra-body tube(s) 130. Intra-body tube(s) 130 enable obtaining measurements of composition of body parts within the body, for example, of the lungs (e.g., to measure edema). Examples of intra-body tube(s) 130 include, an endo-tracheal tube (ETT), a naso-gastric (NG) tube, other feeding tube, a catheter, and/or other tubes designed for insertion into the body, for example, as described with reference to U.S. patent application Ser. No. 16/467,078, U.S. Publication No. 2010/0030133, U.S. patent application Ser. No. 14/986,831, and U.S. patent application Ser. No. 16/000,922, by the same inventors as the present application, incorporated herein by reference in their entirety.

Optionally, computing device 104 is implemented as hardware, for example, circuitry, an assembly of hardware components, an integrated circuit, and/or other architectures. Alternatively or additionally, computing device 104 may be implemented as, for example, a standalone unit, a hardware component, a client terminal, a server, a computing cloud, a mobile device, a desktop computer, a thin client, a Smartphone, a Tablet computer, a laptop computer, a wearable computer, glasses computer, and a watch computer. Computing device 104 may include locally stored software and/or hardware that perform one or more of the acts described with reference to FIG. 2.

Processor(s) 102 of computing device 104 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

As used herein, the term processor may sometimes be interchanged with the term computing device.

Storage device (also known herein as a program store, e.g., a memory) 106 stores code instructions implementable by processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 106 stores code instruction 106A that execute one or more acts of the method described with reference to FIG. 2. Alternatively or additionally, one or more acts of the method described with reference to FIG. 2 are implemented in hardware.

Computing device 104 may include a data repository 116 for storing data, for example, a dataset that stores the impedance measurements obtained from electrodes of different contact components for measurement of body composition of the body portion of the patient, and/or the generated measurements (e.g., body composition values), and/or an indication of the analyzed measurements (e.g., values of clinical parameters), and/or trends in the measurements. Data repository 116 may be implemented as, for example, a memory, a local hard-drive, solid state memory device, a removable storage unit, an optical disk, a storage device, and/or as a remote server and/or computing cloud (e.g., accessed via a network connection).

Computing device 104 includes and/or is in wired or wireless communication with a user interface (and remote storage-processor such as cloud) 118 that includes a mechanism for a user to enter data (e.g., patient information) and/or view presented data (e.g., measurements of composition for different body parts optionally in a GUI). Exemplary user interfaces 118 include, for example, one or more of, a touchscreen, a display, a keyboard, a mouse, and voice activated software using speakers and microphone. External devices communicating with computing device 104 may be used as user interfaces 118, for example, a smartphone running an application may establish communication (e.g., cellular, network, short range wireless) with computing device 104 using a communication interface (e.g., network interface, cellular interface, short range wireless network interface).

Computing device 104 includes device interface 110 that provides electrical communication with one or more controllers 108. Device interface 110 may be implemented as, for example, a network interface card, a hardware interface card, a wireless interface, a physical interface for connecting to a cable, a virtual interface implemented in software, communication software providing higher layers of connectivity (e.g., application programming interface (API), software development kit (SDK), and/or other implementations.

Computing device 104 may include a network interface 120 for connecting to a network 122, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 104 may communicate using network 122 (or another communication channel, such as through a direct link (e.g., cable, wireless) and/or indirect link (e.g., via an intermediary computing device such as a server, and/or via a storage device) for example, with client terminal(s) 124 and/or server(s) 126. For example, server(s) 126 may receive the data collected from the electrodes 118 by the controller 108, and compute the composition of the corresponding body portion(s) of the patient. Server(s) 126 may provide centralized computation services to multiple remote controllers 108 (and/or remote computing devices 104). Server(s) 126 may analyze the data, for example to detect an indication of abnormality and/or predict a future abnormal composition, for example, by a machine learning model that is trained using data obtained from multiple sample patients (e.g., via respective remote computing devices 104 and/or controller 108). Client terminal(s) 124 may connect to server(s) 126 and/or computing device 104 over network 122. For example, the image computed by server(s) 126 using data collected by the computing device 104 is provided for presentation on a display of client terminal(s) 124. In another example, computing device 104 and/or server(s) 126 may obtain additional data of the patient, for example, measurements made by other modalities, imaging results obtained from other imaging modalities, and/or medical history data obtained from an electronic medical record of the patient. The additional data may be used to analyze the measured composition body portion(s) of the patient, for example, to improve accuracy of detecting and/or predicting certain clinical states, such as edema.

Referring now back to FIG. 2, at 202, a setup of the system is provided and/or selected.

One or more different parameters of the system may be selected and/or adjusted, as follows:

Optionally, the number of contact components is selected. The number of contact components may be selected according to the number and/or location of body components being monitored and/or measured. Each contact component is positioned at the outer ends of the respective body segment being monitored and/or measured. Body segments may overlap one another, enabling the same contact component to be used for different body segments, reducing the number of electrodes used for monitoring.

The contact components are independent physical structures, which may be independently positioned at different locations of the body. The contact components are placed spaced apart. Positioning one contact component at one body part may be done without affecting the position of other contact components at other body parts, since the contact components are not physically connected, apart from a flexible busbar.

Each contact component includes multiple electrodes for contacting the body of the patient, optionally the skin. Optionally, each contact component includes three electrodes, optionally arranged along a long axis of the contact component.

Optionally, each contact component is associated with a unique address. All electrodes of the contact component may be selected by the same unique address. The electrodes of the contact component having the unique address may be independently operated (e.g., as a current source, current sink, voltage sensor and other biosensor) by instruction issued by the controller to the unique address of the contact component. Alternatively, each electrode is associated with an electrode structure having its own unique address recognized by an address decoder. Each electrode may be independently operated by the controller providing operating instructions to the unique address of the respective electrode.

Optionally, each contact component includes a connector for connecting to the busbar, optionally reversibly, enabling detachment from the busbar. Contact components may be added (i.e., connected) and removed (i.e., detached) from the busbar as desired, for example, to monitor different body segments on different patients. Alternatively, the busbar is pre-attached to the contact component in a manner where contact components cannot be removed from the busbar without cutting the connection.

Optionally, the number of busbars is selected. Optionally, at least one busbar is connected to two or more electrodes (or electrode structures) of two or more contact components. Electrodes may be selected and operated using the same common busbar via an address of the target electrode (and/or target contact component). Optionally, a single main busbar is used, where all contact components are connected to the main busbar. Alternatively, two or more busbars are used, for example, one busbar connecting to contact components on the left side of the patient, and another busbar connecting to contact components on the right side of the patient.

Optionally, one or more intra-body probes, optionally tubes, for insertion into the body of the patient are selected and/or designated. The intra-body tube is coupled and/or includes thereon one or more contact components with multiple electrodes, or the electrodes and associated circuitry when the tube itself acts as the contact component (i.e., the term contact component may refer to the tube). The electrodes and/or contact component of the tube is connectable to one of the busbars, and addressable by the controller, as described herein. Optionally, a busbar connects to the electrodes (i.e., the contact component) of the tube and to one or more other contact components positioned externally t the body of the patient (e.g., on the skin). Exemplary contact components include: endotracheal tube (ETT), feeding tube, and naso-gastric (NG) tube, for example, as described with reference to U.S. patent application Ser. No. 16/467,078, U.S. Publication No. 2010/0030133, U.S. patent application Ser. No. 14/986,831, and U.S. patent application Ser. No. 16/000,922, by the same inventors as the present application, incorporated herein by reference in their entirety. Current and/or voltage may be measured between an electrode on the tube and another electrode on a contact component on the surface of the body of the patient, for example, impedance measurements performed by electrodes of the tube and a skin contacting contact component is indicative of body composition of a lung, such as an amount of fluid in the lung and/or type of fluid in the lung.

Optionally some of the electrodes are connected to controller via the addressing busbar while some are individually connected and assigned to the controller via conductors i.e., a mixed interface connection of electrodes and other bio sensing elements.

Figure 3:
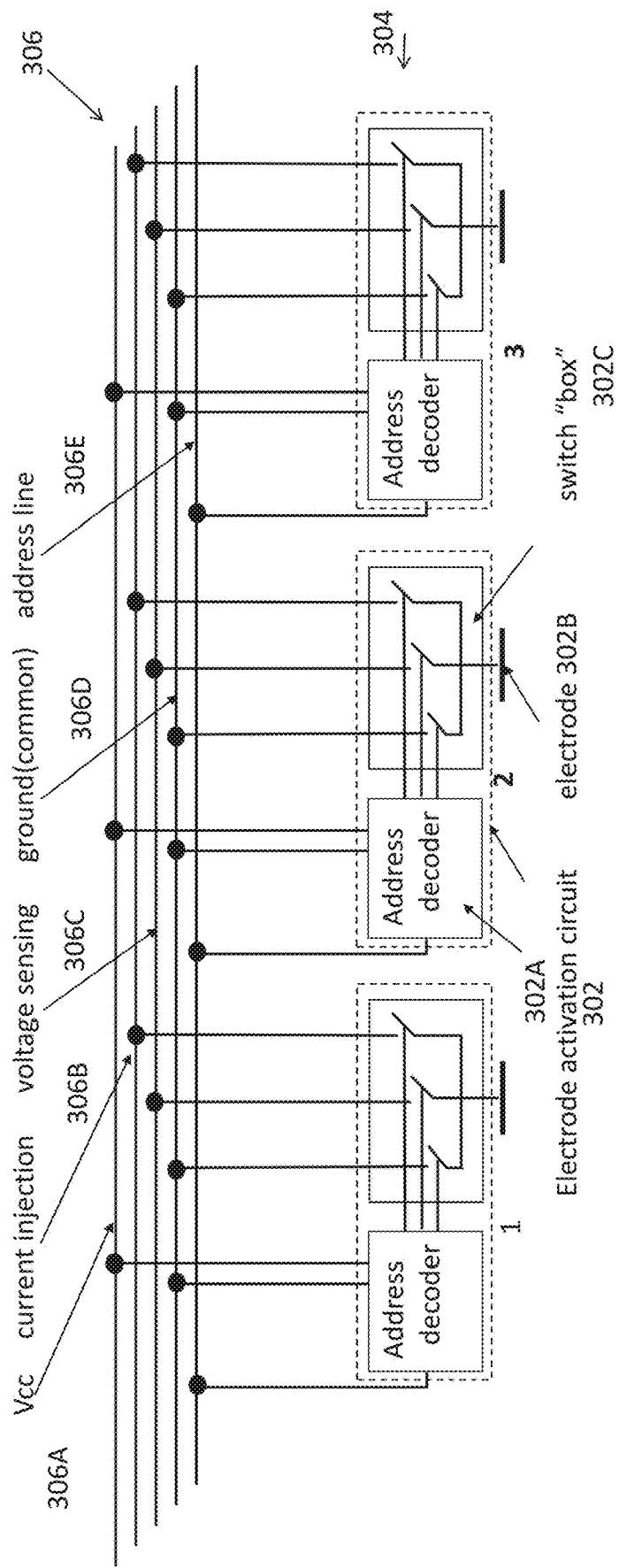
FIG. 3 is a schematic depicting an exemplary architecture of an addressable electrode components, in accordance with some embodiments of the present invention.

Reference is now made to FIG. 3, which is a schematic depicting an exemplary architecture of an addressable electrode components 302 (also referred to as electrode activation circuit), in accordance with some embodiments of the present invention. In an exemplary implementation, multiple electrode components 302 are part of a contact component 304, optionally three electrode components 302 along a long axis of contact component 304, as descried herein.

Each electrode component 302 may include an address decoder sub-component (e.g., circuitry) 302A for identifying the unique address of the respective electrode component 302 transmitted on the multi conductor busbar 304, an electrode 302B which is operable to transmit current, receive current, and/or measure voltage, and a switch sub-component 302C (e.g., circuitry) that connects the electrode 302B to the relevant line of a multi conductor busbar 306 in response to triggering by the address decoder 302A recognizing the unique address on the address line of the multi conductor busbar 306. Additional optional sub-components of electrode component 302 include an amplifier for amplifying the measurement (e.g., voltage, current) by the electrode or other optional sensors 302B, and/or a sub-component that obtains implements instructions for operation of the electrode 302B received from the relevant line of the multi conductor busbar 306, for example, operating electrode 302B as the current source, current receiver, and/or voltage sensor.

Multi conductor busbar 306, which is connected to the controller, may include one or more of the following sub-components (e.g., as conduction lines) each for a dedicated task: Vcc line 306A for transmission of power to the electrode components 302, current injection line 306B for transmission of a current to the electrode operating as current source, voltage sensing line 306C for receiving voltage measurements by an electrode operating as a voltage sensor, ground 306D for acting as a global ground, and address line 306E for transmitting the unique address for selection and operation of a certain electrode structure. Additional optional lines include an instruction line for transmitting instructions for the operation mode of the electrode having the unique address (e.g., current source, current sink, voltage sensor) and/or for a current reception line for receiving current received by the electrode operating as the current sink and lines connecting other sensors.

Figure 4:
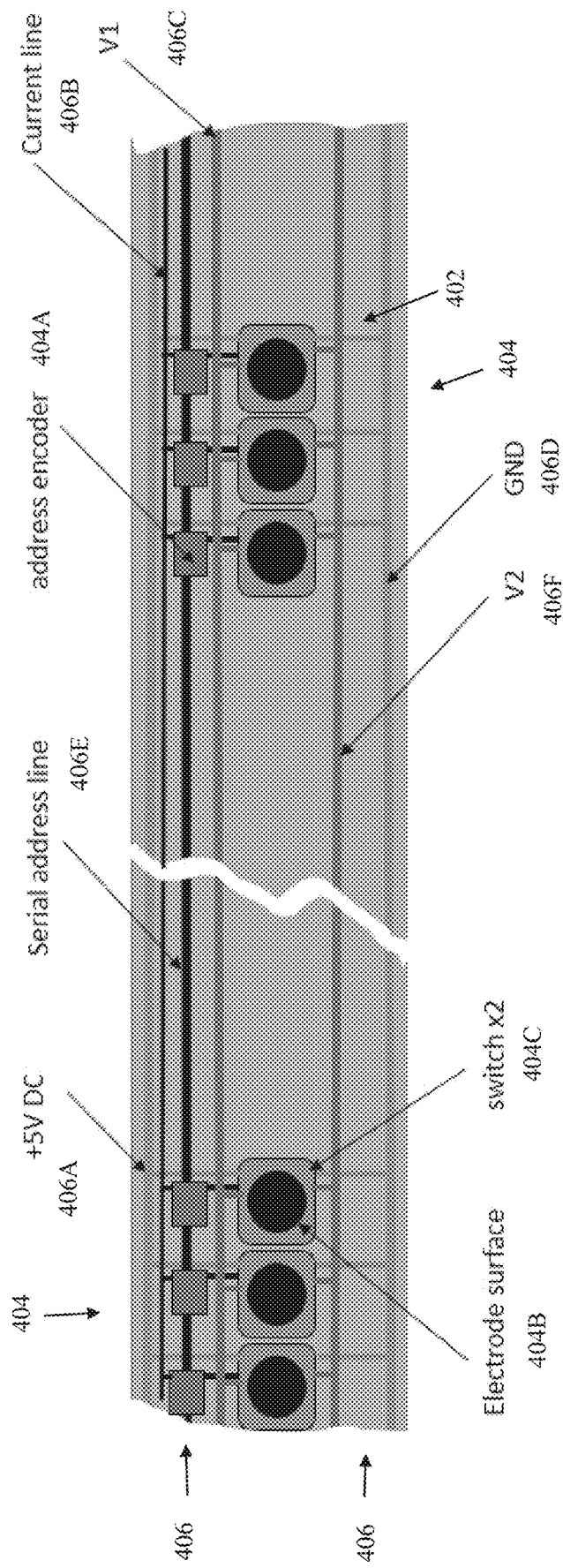
FIG. 4 is a schematic of an exemplary implementation of two contact component coupled to the same multi conductor busbar, in accordance with some embodiments of the present invention.

Reference is now made to FIG. 4, which is a schematic of an exemplary implementation of two contact component 404 coupled to the same multi conductor busbar 406, in accordance with some embodiments of the present invention. Optionally, multiple contact components and the busbar are integrated into a single physical structure, optionally a long strip, for example, made of flexible printed circuit board, where each contact component may be independently positioned at different parts of the body. Each contact component 404 includes three electrode components 402, each including an electrode 404B, one or more switches 402C, an address encoder 404A and other optional components as described herein. The busbar 406 includes a +5V DC line 406A, serial address line 406E, current line 406B, V1 line 406C, V2 line 406F, and ground line 406D.

As used herein, the term electrode component may sometimes be interchanged with the term electrode, for example, when each electrode is addressable.

Referring now back to FIG. 2, at 204, the contact components are attached to the body of the patient. Contact components may be attached, for example, by an adhesive surface which sticks to the skin of the patient. Electrodes located beside the adhesive surfaces are placed in contact with the skin. In another example, contact components are attached via an outer and/or external connector, for example, wrapping a bandage around the contact component and limb, or placing the contact component between a pressure stocking and the leg of the patient. Tubes acting as contact components (or having contact components attached thereon) may be inserted into the body of the patient.

Optionally, the busbar is connected to the contact components, before and/or after attaching the contact components to the body of the patient. Alternatively, the busbar is pre-attached to the contact components. The busbar may be flexible, enabling use of patients of different sizes.

Optionally, the electrodes (e.g., three) arranged along a long axis of each contact component are arranged and positioned on the patient along an imaginary straight line drawn on the surface of the body of the patient. For example, along an imaginary line running from the heel to the wrist, the contact component is positioned along its long axis parallel to this imaging line, for example, on the ankle (e.g., in a direction from the feet to the head), and on the wrist (e.g., in a direction from the palm to the elbow).

The placement of the electrodes along the imaging line enables the controller, for example, to inject current and receive current using a middle electrode of each contact component of a pair contact component along boundaries of a body segment, and to measure voltage using inner facing electrodes of the pair of contact components. When a different body segment is monitored using one of the contact components already used for another body segment, the current is again injected and received using the middle electrodes, and voltage is measured using the inner facing electrodes, where one of the currently inner facing electrodes may have served as an outer acing electrode for measuring the other body segment. For example, placing contact components on the wrist, ankle, and chest, enable using three electrodes on three contact components to measure the following segments: wrist-chest, chest-ankle, and wrist-ankle. The electrodes and contact component of the chest enable measuring the wrist-chest and chest-ankle segments as separate segments that are in contact with one another.

By another option current is injected to the two extreme electrodes wrist to ankle and voltage is sensed from individual body segments.

Optionally, the human body may be considered as empirically composed of the following segments, each having a uniform electric conductivity: four limbs (left arm, right arm, left leg, right leg), and the trunk. Contact components may be positioned for measurement of impedance of one or more of the segments.

Exemplary locations for placement of the contact component includes: wrist, ankle, chest, metacarpal line, metatarsal line, elbow, shoulder, armpit, knee, hip, neck, along midaxillary line, along midclavicular line, and the like.

Figure 5:
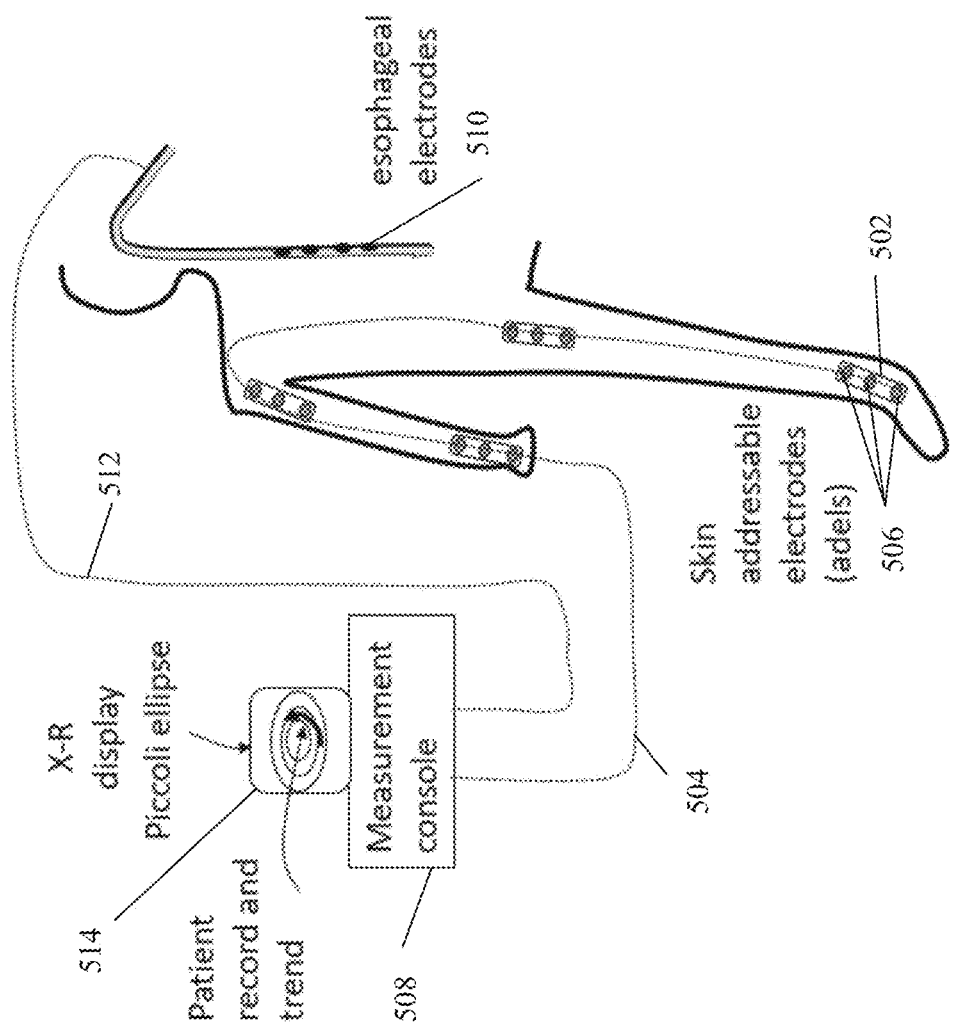
FIG. 5 is a schematic depicting placed contact components, which are independently addressable over a common multi conductor busbar, for monitoring multiple body segments of a patient, in accordance with some embodiments of the present invention.

Reference is now made to FIG. 5, which is a schematic depicting placed contact components 502, which are independently addressable over a common multi conductor busbar 504, for monitoring multiple body segments of a patient, in accordance with some embodiments of the present invention. Contact components (one is marked as 502 for clarity) are shown as placed on the wrist, shoulder, thigh, and ankle, as a not necessarily limiting example. Each contact component 502 includes three electrodes 506 arranged along a long axis of the respective contact component. A measurement console 508 acts as a controller for operating the electrodes 506 of the contact components 502 via addressable instructions transmitted over the common busbar 504. Impedance measurements are analyzed and may be presented on a display 514, for example as a Piccoli ellipse and/or depicting trend arrow superimposed on the Piccoli chart. Optionally, electrodes 510 are located within the esophagus, for example, positioned on a feeding tube. Electrodes 510 may be used to measure impedance of internal segments, for example, the lungs, as described herein. Electrodes 510 may be connected to main busbar 504 or to another busbar 512. Electrodes 510 may be independently addressable and/or operated by the controller, as described herein.

Figure 6:
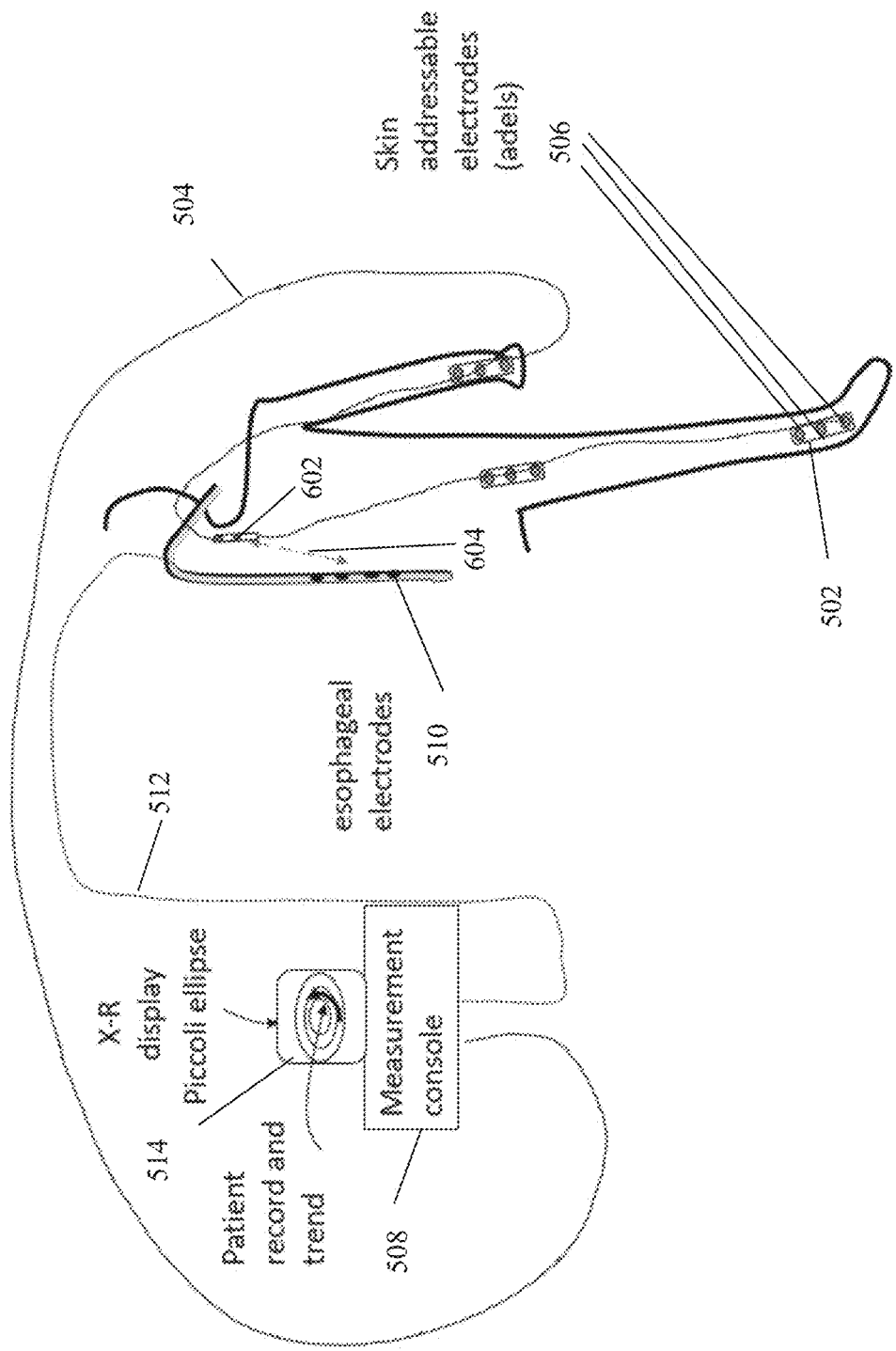
FIG. 6 is a schematic based on the setup described with reference to FIG. 5, including an additional contact component with electrodes thereon positioned for measuring of impedance for estimation of cardiac output, in accordance with some embodiments of the present invention.

Reference is now made to FIG. 6, which is a schematic based on the setup described with reference to FIG. 5, including an additional contact component 602 with electrodes thereon positioned, for example, for measuring of impedance for estimation of cardiac output (as denoted by arrow 604), in accordance with some embodiments of the present invention and or lungs water content. Contact component 602 may be positioned in proximity to and/or above the heart of the patient, for example, at the base of the neck as shown. Impedance measured using electrodes of contact component 602 and electrodes 510 located within the esophagus may be analyzed for computation of cardiac output using bioimpedance cardiography in a non-invasive or minimally invasive manner, which may perform better as a trend analysis of cardiac output in comparison to standard approaches that measure absolute cardiac output (e.g., using sensors placed within the heart and/or the circulatory system). The setup depicted is a four-terminal impedance monitoring (with one terminal as address) setup.

Figure 7:
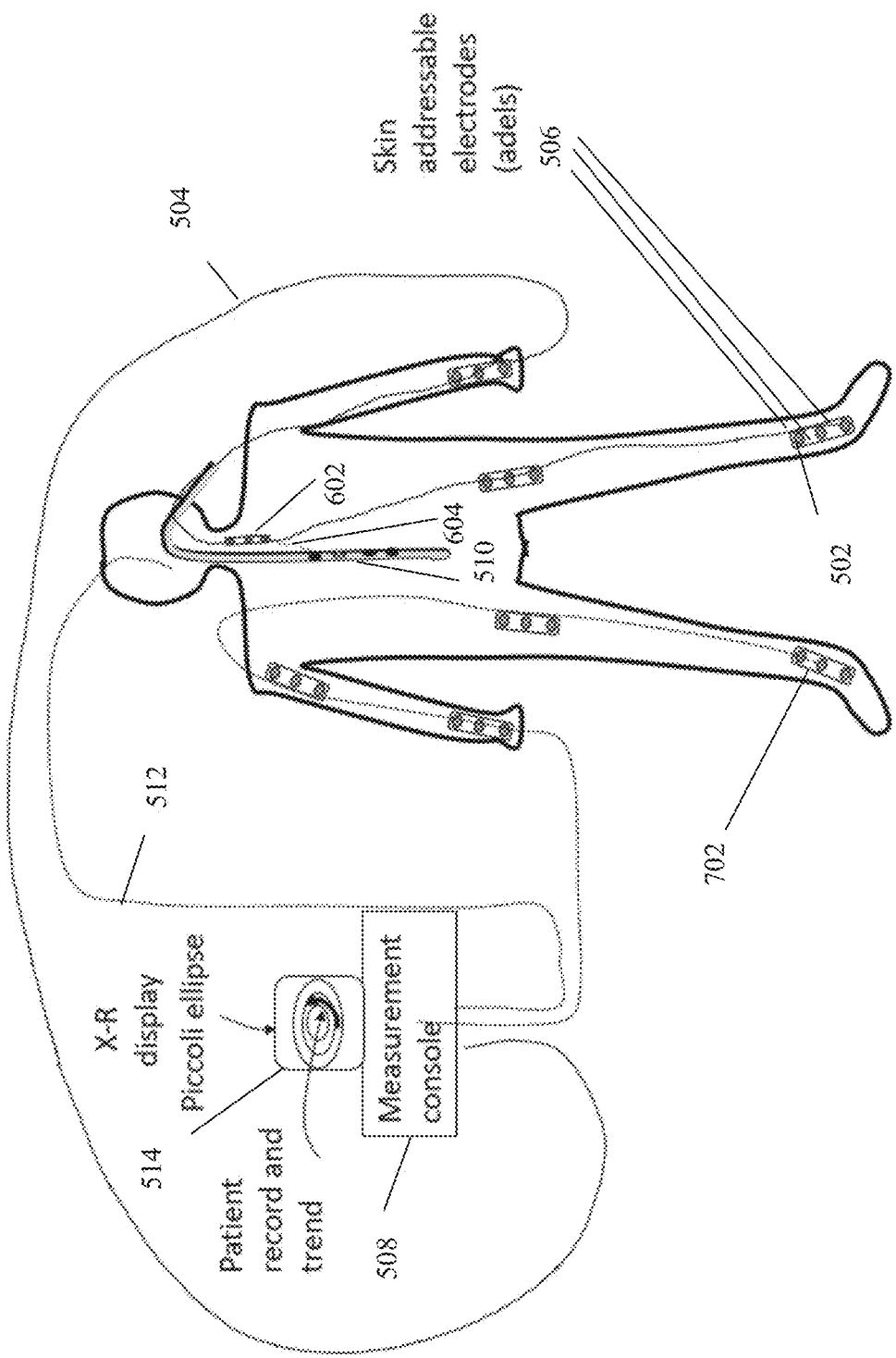
FIG. 7 is a schematic based on the setup described with reference to FIG. 6 (and FIG. 5), including additional contact components located on the left side of the patient's body, in addition to the contact components positioned on the right side of the patient's body as in FIGS. 5 and 6, in accordance with some embodiments of the present invention.

Reference is now made to FIG. 7, which is a schematic based on the setup described with reference to FIG. 6 (and FIG. 5), including additional contact components (one contact component 702 labelled for clarity) located on the left side of the patient's body, in addition to the contact components positioned on the right side of the patient's body as in FIGS. 5 and 6, in accordance with some embodiments of the present invention. Positioning the electrodes on both sides of the patient's body and optionally inside the patient (e.g., in the esophagus) enables measuring impedance in many different body segments defined by end pairs of selected contact components, on either side of the body and/or in the middle of the body (e.g., between a contact component on the left side and another contact component on the right side).

Figure 8:
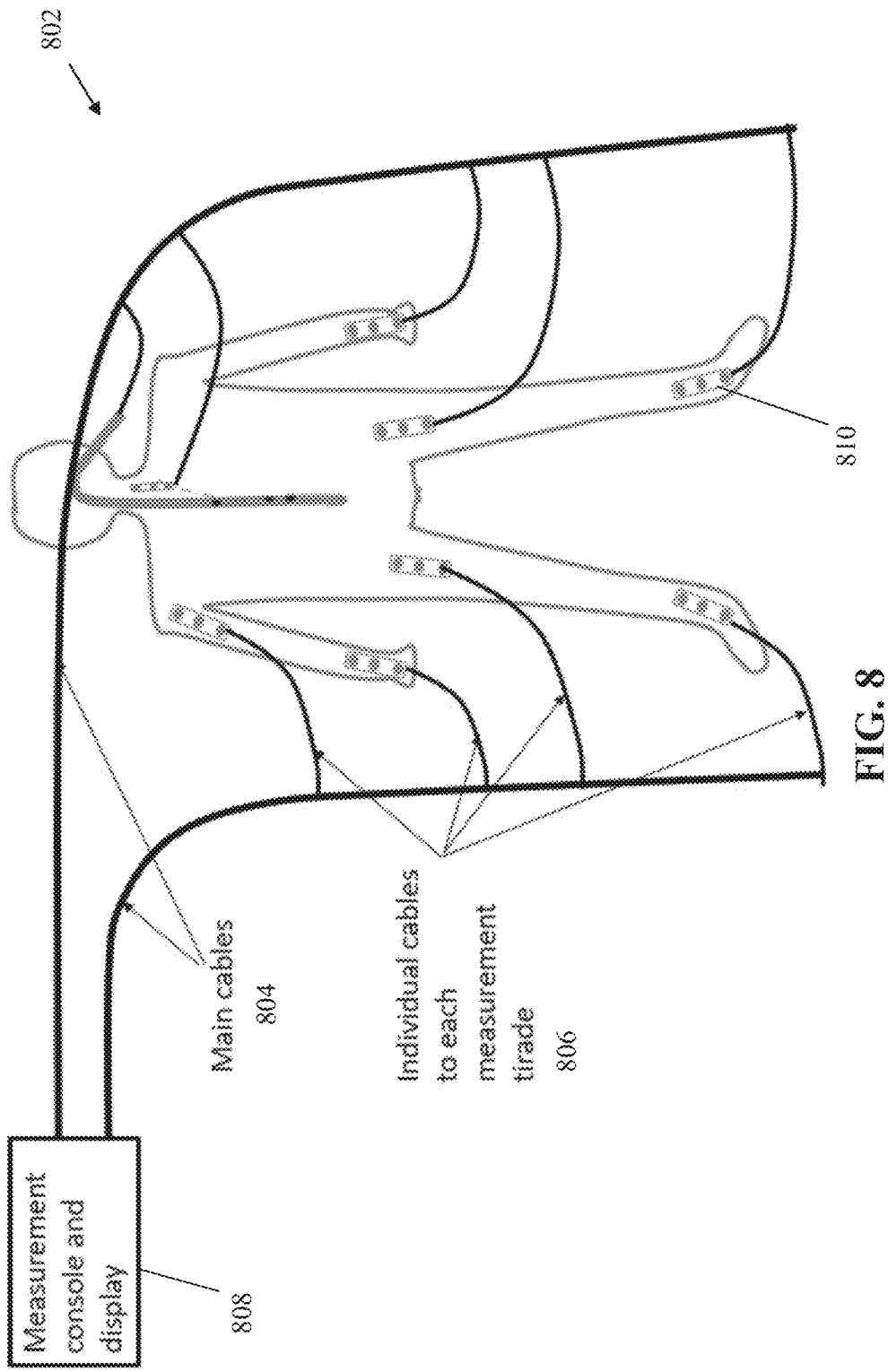
FIG. 8 is a schematic of an architecture in which each contact component is connected to a main multi conductor busbar via an individual cable, in accordance with some embodiments of the present invention.

Reference is now made to FIG. 8, which is a schematic of an architecture 802 in which each contact component (one contact component 810 labelled for clarity) is connected to a main multi conductor busbar 804 via an individual cable 806, in accordance with some embodiments of the present invention. A controller 808 transmits instructions to (and receives measurements from) selected contact components via the address of the respective contact component over main busbar 804 and the individual cables 806. A single main busbar 804 may be used, or two or more main busbars, for example, one busbar connecting to cables of contact components located on the left side of the body, and another busbar connected to cables of contact components located on the right side of the body. The electrodes on the tube within the body (e.g., on the feeding tube located within the esophagus) are connected to one of the main busbars. Contact components may be positioned on both sides of the body as described with reference to FIG. 7, and as described herein, portion of the electrodes are connected to a busbar capable of addressing while others may be connected individually in a more conventional way.

Figure 9:
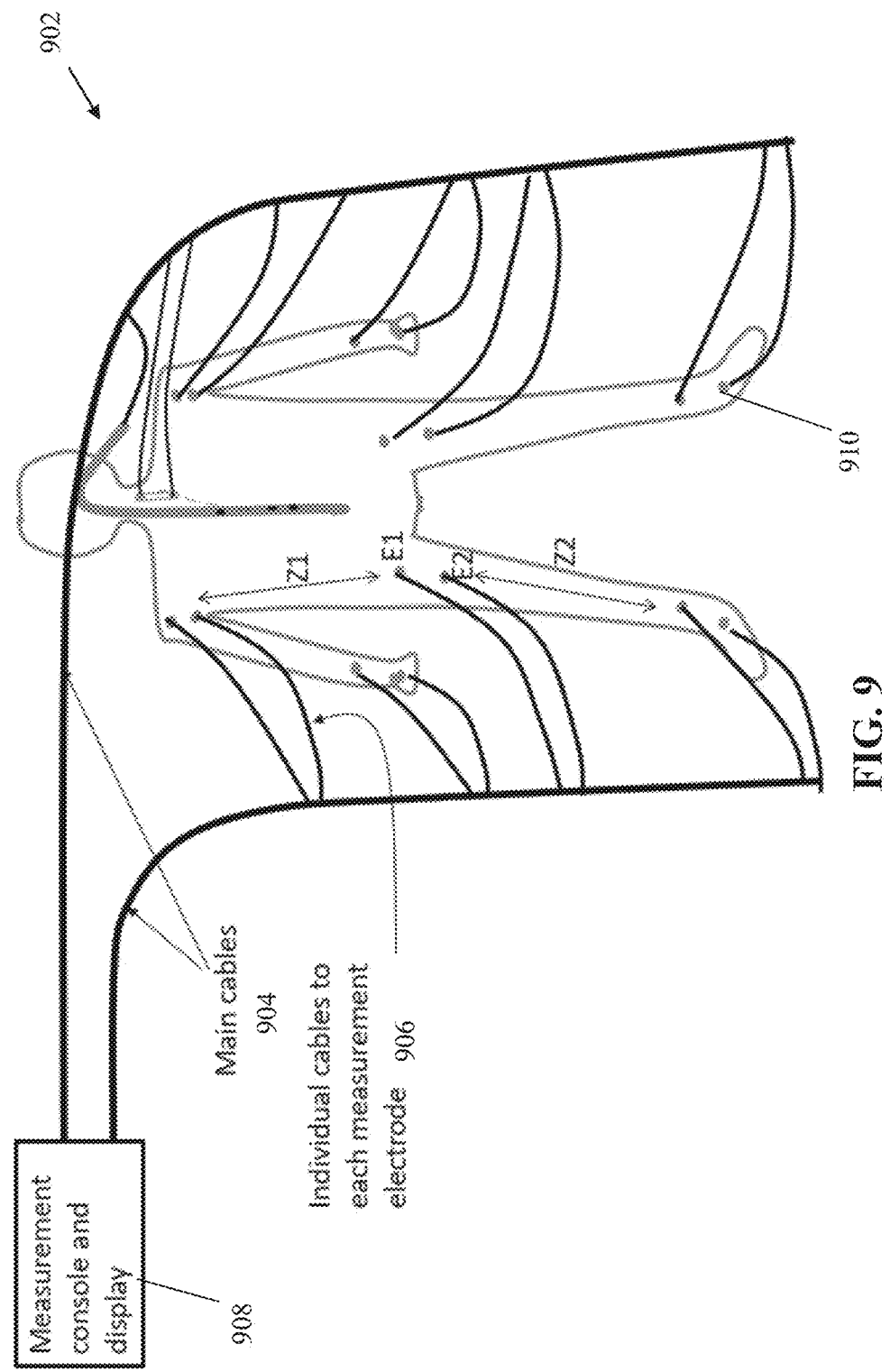
FIG. 9 is a schematic of an architecture in which each electrode is connected to a main multi conductor busbar via an individual cable, in accordance with some embodiments of the present invention.

Reference is now made to FIG. 9, which is a schematic of an architecture 902 in which each electrode (one electrode 910 labelled for clarity) is connected to a main multi conductor busbar 904 via an individual cable 906, in accordance with some embodiments of the present invention. Each electrode 910 may be associated with its own contact component, multiple electrodes 910 may be associated with a single contact component (e.g., two, three or more electrodes per contact component), or electrodes 910 are directly placed on the patient without the contact component. Each electrode 910 may be part of an electrode component that includes addressing circuitry for recognizing the unique address of the respective electrode, as described herein. A controller 908 transmits instructions to (and receives measurements from) selected electrodes via the address of the respective electrode component over main busbar 904 and the individual cables 906. Each electrode may be instructed to operate in a selected operating mode (e.g., current source, current sink, and/or voltage measurement sensor or other biosensor) according to the instructions and associated address of the selected electrode transmitted by the controller 908 over the main busbar 904. A single main busbar 904 may be used, or two or more main busbars, for example, one busbar connecting to cables of electrode components located on the left side of the body, and another busbar connected to cables of electrode components located on the right side of the body. The electrodes on the tube within the body (e.g., on the feeding tube located within the esophagus) are connected to one of the main busbars. Electrode components may be positioned on both sides of the body. For example, for measuring an impedance Z1, electrode E1 is instructed to operate as a voltage sensor and electrode E2 is instructed to operate as a current electrode. In another example, for measuring another impedance Z2, electrode E1 is instructed to operate as a current electrode and E2 is instructed to act as measurement electrode. It is noted that in order to measure impedance, the electrode transmitting and/or receiving current is located behind the electrode measuring voltage such that the current, as it travels to and/or from the current electrode, passes by the electrode sensing voltage. The contact component with three spaced apart electrodes arranged a long axis is designed to improve measurement of impedance by the relative placement of the current and voltage operated electrodes, as described herein.

Figure 10:
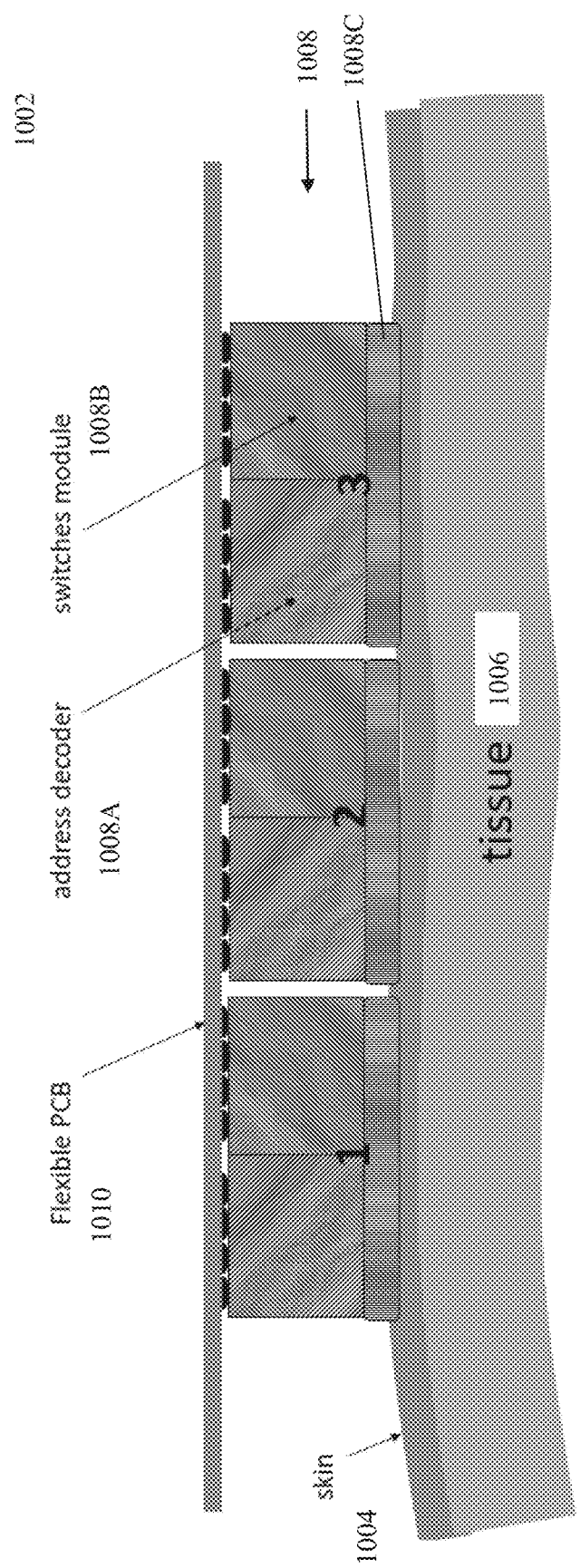
FIG. 10 is a schematic depicting an exemplary contact component placed in contact with a skin of a patient for measuring of impedance of a body segment including tissue, in accordance with some embodiments of the present invention.

Reference is now made to FIG. 10, which is a schematic depicting an exemplary contact component 1002 placed in contact with a skin 1004 of a patient for measuring of impedance of a body segment including tissue 1006, in accordance with some embodiments of the present invention. Contact component 1002 includes three electrode components 1008 (sometimes also referred to as electrodes) arranged along a long axis of the contact component 1002. Contact component 1002 may include a support strip 1010 that connects to electrode components 1008, for example, as a flexible printed circuit board, plastic, cloth, textile and/or other material. Each electrode component 1008 may include an address decoder 1008A, electrode 1008B, and switch(es) 1008C, as described herein.

At 206, a body segment is selected for measurement of impedance thereof. Each body segment may be sequentially measured. Optionally, the most inner/smallest segments are selected first, followed by larger segments that include and/or overlap the inner/smaller segments. For example, first the wrist-chest segment, followed by the chest-ankle segment (or vice versa), followed by the wrist-ankle segment.

Alternatively, the larger segments are measured first, followed by the smaller segments which may be located and/or overlap with the larger segment. For example, first the wrist-angle segment, followed by the wrist-chest and/or chest-ankle segment. Optionally, the selected segments are located within the body, for example, the lung and/or the heart (e.g., for estimation cardiac output using impedance cardiography as described herein). The internal segments may be measured using electrodes positioned within the body on probes (e.g., tubes), for example, on a nasogastric tube positioned within the esophagus, as described herein.

Figure 11:
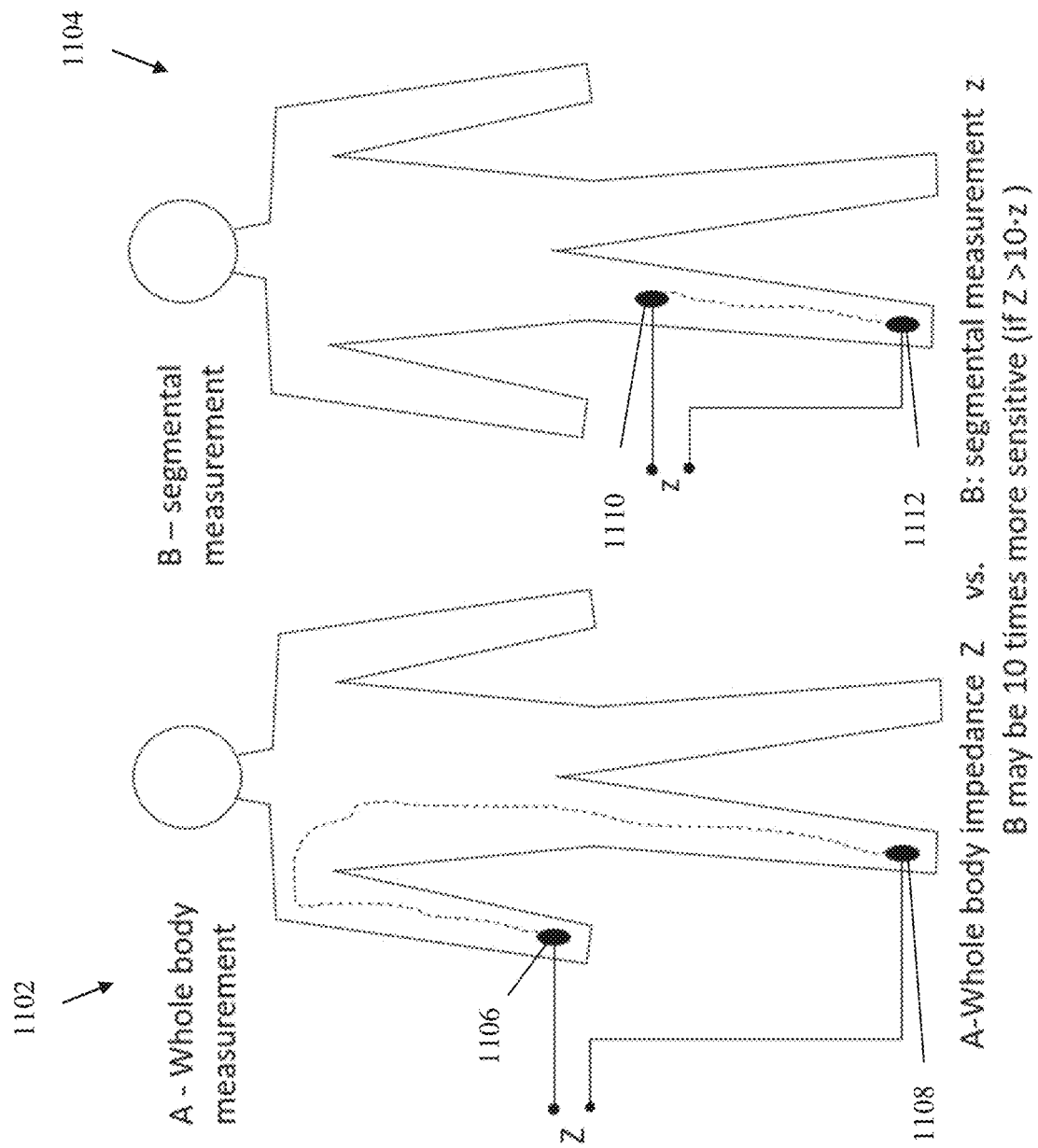
FIG. 11 is a schematic depicting an example of a measurement of a whole body segment and a measurement of a leg segment, to help understand some embodiments of the present invention FIG. 12 includes Piccoli diagrams for a whole body measurement and for a body segment, to help understand improved accuracy of impedance measured for the body segment in comparison to the whole body.

Reference is now made to FIG. 11, which is a schematic depicting an example of a measurement of a whole body segment 1102 and a measurement of a leg segment 1104, to help understand some embodiments of the present invention. Impedance of the whole body (denoted Z) may be measured, for example, by an electrode 1106 placed at a wrist and another electrode 1108 placed at an ankle. Impedance of the leg segment (denoted z) may be measured, for example, by an electrode 1110 placed at an upper part of the leg (e.g., thigh, hip) and another electrode 1112 placed at the ankle of the leg. The impedance measured for a body segment (e.g., for the leg as in 1104) may be 10 time more sensitive than impedance measured for the whole body (e.g., as in 1102). It is noted that values obtained using the setup depicted in 1102 correspond to BIVA type impedance measurements.

Reference is now made to FIG. 12, which includes Picccoli diagrams for a whole body measurement 1202 and for a body segment 1204, to help understand improved accuracy of impedance measured for the body segment in comparison to the whole body. Piccoli diagram 1202 for the whole body, which may be using the whole body segment measurement setup 1102 of FIG. 11, depicts angular change due to local impedance change denoted $\alpha_A$. Piccoli diagram 1204 for the body segment, which may be using the leg body segment measurement setup 1104 of FIG. 11, depicts angular change due to local impedance change denoted $\alpha_B$. The increase in sensitivity of segmental measurement over whole body measurement is denoted as $\alpha_A \gg \alpha_B$.

At 208, the controller selects and activates and/or operates a pair of contact components (and/or electrodes thereof) connected by a common multi conductor busbar. Electrodes on each of the contact components may be selected and activated and/or operated. Selection and activation and/or operation may be sequential, for example, first one member of the pair, followed by the second member of the pair.

Exemplary operation modes may include: current source, current sink, voltage sensor and other biosensor.

The controller generates and transmits instructions for activation and/or operation of the certain contact component (and/or electrode thereof) by transmitting the unique address of the certain contact component (and/or electrode thereof) on the busbar, for example, on an address line component of the busbar. Instructions for operation in a certain operation mode may be transmitted in association with the unique address, for example, on another line component of the busbar. Circuitry of the contact component corresponding to the unique address implement the instructions (e.g., to operate in the designated operation mode).

Other contact components (and/or electrode components) may listen to the busbar for their address and ignore the instructions when the address is not assigned to them. Addressing may be defined, for example, by a set of sequential and/or parallel signal bits transmitted over the busbar (e.g., over the dedicated address line component of the busbar).

At 210, one or more impedance measurements of the selected body segment are obtained from the pair of contact components (i.e., from electrodes thereof). Optionally, voltage and current measurements are obtained from the pair of contact components. The impedance measurement is computed from the obtained voltage and current measurement.

The applied current may be an alternating current (AC) and/or direct current (DC).

Optionally, as another embodiment, the electrodes and/or sensors may be mounted inside an inner wall of a sleeve (e.g., made from textile, plastic, and/or other materials or material combination) having optionally a double wall. The sleeve may be applied on a patient's body part. In use, when the sleeve is placed on the body, the electrodes contact the body of the patient, optionally the skin. Electrode components are connected via the busbar and optional cable to the controller, as described herein. The lumen formed by the double wall may be inflated. The inflated lumen may increase probability and/or guarantee substantially uniform equal pressure on all electrodes for more uniform measurements. Inflation may be controlled by the controller via a pump connected to an inflation tube of the sleeve.

Optionally multiple sensor strips may be applied on the patient's body part by adhesive enabling, for example, in both embodiments 3D impedance mapping of the body part.

Figure 18:
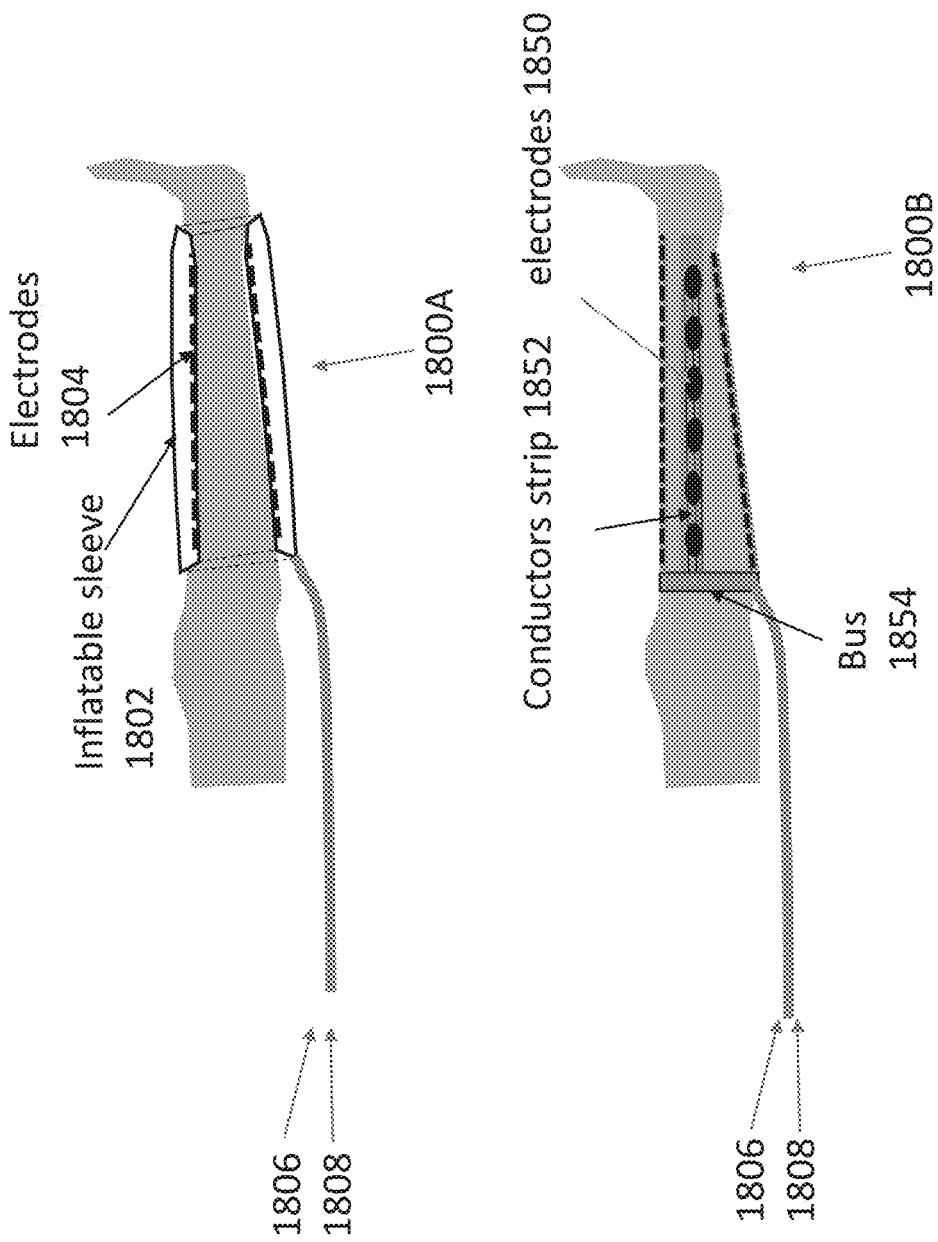
FIG. 18 includes a schematic of a cross section of a foot of a patient an inflatable sleeve with electrodes and a schematic of a cross section of a foot with electrodes on conductor strips, in accordance with some embodiments of the present invention.

Reference is now made to FIG. 18, which includes a schematic 1800A of a cross section of a foot of a patient an inflatable sleeve 1802 with electrodes 1804 located within the inner wall of the sleeve, in accordance with some embodiments of the present invention. Sleeve 1802 includes a busbar 1806 and/or inflation tube 1808 which connect to a controller, as described herein. FIG. 18 also includes a schematic 1800B of a cross section of a foot with electrodes 1850 on conductor strips 1852 (e.g., spaced apart electrodes on contact components), in accordance with some embodiments of the present invention. There may be multiple conductor strips 1852 connected to a single main busbar 1854. Each strip 1852 of electrodes 1850 may be independently positioned on the leg by an adhesive. It is noted that schematics 1800A and 1800B may be combined, where strips of electrodes are positioned within the inflatable sleeve, for example, using Velcro, straps, and/or other connecting materials.

Optionally, multiple impedance measurements are obtained, optionally at different current frequencies-multi frequency, for example, in the range of about 10 Hz, 100 Hz 1000 Hertz (Hz) to 100 kiloHertz (kHz), or 1 kHz to 1000 kHz, optionally using a center frequency of 50 kHz. Exemplary frequencies include: 1 kHz, 5 kHz, 50 kHz, 250 kHz, 500 kHz, and 1000 kHz. Frequencies may be in increments of, for example, 1 kHz, 10 kHz, or other values, or continuous measurements with continuous variation of frequency. A 3D map may be created and presented using a linear graduate measurement of the different frequencies, as described herein.

Current (e.g., AC and/or DC) may be sinusoidal shaped or other pattern.

Current amplitude may be, for example, about 10, 100, or 200, or 400, or 1000 microamperes, or other values.

An exemplary current used for the estimation of FFM is an alternating sinusoidal electric current of 400 μA at a single operating frequency of 50 kHz.

Optionally, the computed impedance is a complex value. The real part (denoted R) and the imaginary part (denoted X) may be computed.

The impedance is indicative of an estimation of body composition of the selected body segment.

At 212, one or more features described with reference to 206-210 are iterated. Optionally, the iterations are for obtaining impedance measurements of different body segments, and/or for monitoring impedance values of the same body segments(s) over time by obtaining multiple impedance values over a time interval.

Optionally, the controller iteratively switches between different pairs of contact components of different body segments to obtain impedance measurements over a time interval for monitoring each of the body segments. For example, one or more impedance measurements are obtained for one body segment, then another set of impedance measurements is obtained for another body segment, where the cycle of measurements for the first and the second body segment are iterated over time.

Optionally, smaller segments are measured first. Larger segments, which include two or more smaller segments therein, may be measured later. Alternatively, first larger segments are measured, and then two or more smaller segments located within the larger segments are measured.

Alternatively, a single segment is selected for monitoring, for example, for monitoring hydration level of a lower leg. Contact components of other segments may be electrically decoupled or otherwise not activated by the controller.

Optionally, the controller iteratively selects another (e.g., second) pair of contact components from the set of contact components connected by the common multi conductor busbar. The contact component of the first pair of contact components may be positioned between the second pair of contact component. For example, the first pair of contact components are located on the wrist and along the midaxillary line, and the second pair of contact components are located on the wrist (i.e., the same wrist component as in the first pair) and on the ankle. Alternatively, the first and second pairs are switched. The first and second pair of contact components are connected to the same common multi conductor busbar.

Optionally, when contact component of the first pair are positioned between the second pair of contact component, the electrodes of the first pair are non-selected and not activated during the impedance measurement performed for the respective body segment located between the second pair of contact components. One of the second pair of contact components may be selected from the first pair of contact components. For example, when the first pair measures impedance of the body segment between the wrist and chest, and the second pair measures impedance of the body segment between the wrist and ankle, the contact components positioned on the chest (i.e., between the wrist and ankle) is not selected and not activated during impedance measurements of the body segment between the wrist and ankle. The wrist contact components may be used for impedance measurements of both the wrist-ankle and wrist-chest body segments.

Optionally, for the architecture of the contact component including three (or more) electrodes optionally aligned along a long axis of the contact component, where all electrodes of the multiple contact components are optionally aligned along an imaginary straight line drawn on the skin of the patient (it is noted that the line may be straight along the skin, but curve according to surface features of the skin), the controller may inject and receive current using a middle electrode of each contact component of the first pair and second pair of contact components. Voltage may be measured using inner facing electrodes of the first pair and second pair of contact components. For example, for measuring the wrist-chest and chest-ankle body segments, the middle electrode of the chest contact component is used for current. The electrode of the chest contact component closer to the wrist is used for the wrist-chest segment, and the other electrode of the chest contact component closer to the angle is used for the chest-ankle segment. For the wrist-ankle segment, the chest contact component is unused.

Figure 13:
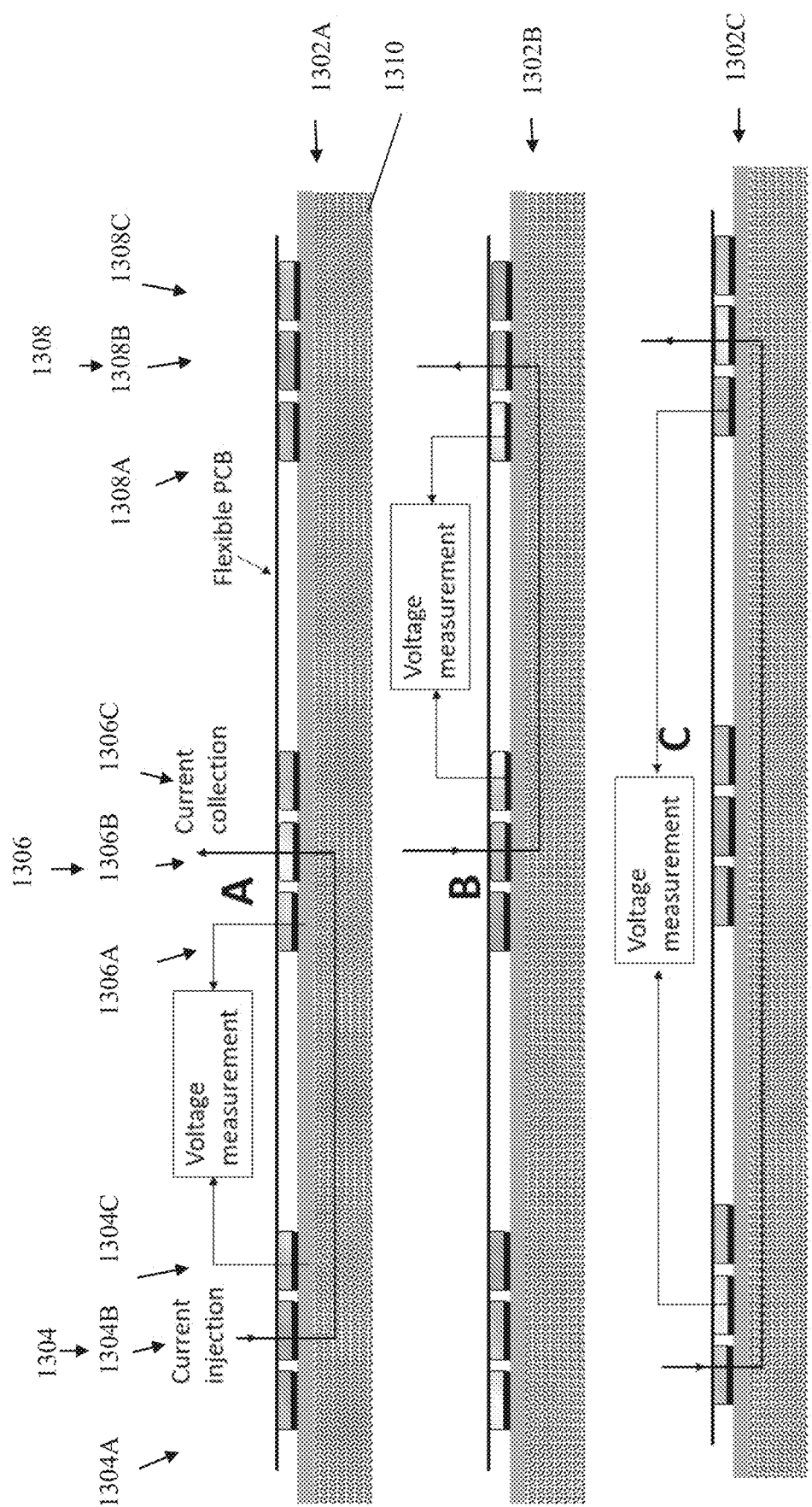
FIG. 13 is a schematic depicting a process of selective activation of electrodes of multiple contact components for sensing multiple body segments, in accordance with some embodiments of the present invention.

Reference is now made to FIG. 13, which is a schematic depicting a process of selective activation of electrodes of multiple contact components for sensing multiple body segments, in accordance with some embodiments of the present invention. The process is executed by instructions transmitted by a controller over a busbar, as described herein. Contact components 1304, 1306, 1308, which are placed against body of patient 1310, each include three respective electrodes 1304A-C, 1306A-C, 1308A-C arranged along a longitudinal line.

Schematic 1302A depicts the process of measuring impedance of the body segment (denoted A) between contact components 1304 and 1306. Middle electrode 1304B is operated as a current injector, and middle electrode 1306B is operated as a current collector, while voltage is measured between inner facing electrodes 1304C and 1306A.

Schematic 1302B depicts the process of measuring impedance of the body segment (denoted B) between contact components 1304 and 1308. Middle electrode 1306B is operated as a current injector, and middle electrode 1308B is operated as a current collector, while voltage is measured between inner facing electrodes 1306C and 1308A.

Schematic 1302C depicts the process of measuring impedance of the body segment (denoted C) between contact components 1304 and 1308. It is noted that body segment C includes both body segments A and B. Outer electrode 1304A is operated as a current injector, and middle electrode 1304 is operated for voltage measurement. Alternatively, middle electrode 1304B is operated as a current injector, and middle electrode 1308B is operated as a current collector, while voltage is measured between inner facing electrodes 1304C and L08A. In either case, the principle of operation is to have two current injecting electrodes and between the two current injecting electrodes there are two voltage sensing electrodes, which is the desired 4 electrodes approach to impedance sensing.

At 214, the obtained impedance data is analyzed. The impedance data may be analyzed over small time intervals (e.g., single measurement of set of closely spaced measurements such as at different frequencies, for example, less than about 1 second, or 10 seconds, or 1 minute) such as to obtain a real time value, analyzed over large time intervals (e.g., about 10, 15, 30, 60, 120 minutes, 6, 12, 24, 48, 72 hours, 1 week, or other values) such as to compute trends.

Optionally, body composition is estimated for each body segment according to impedance values obtained for the respective body segment. Exemplary body composition include fat content, edema, water content, electrolyte content, and pathological status.

Alternatively or additionally, the impedance measurements of one or more body segments are analyzed for determining whether a current target has been reached, for example, whether the body composition of the respective segments reached a clinically significant target. Optionally, an alert is generated when the target has been reached, for example, a pop-up notification on a display, and/or a text message is sent to a mobile device of an on call physician.

Alternatively or additionally, the impedance measurements of one or more body segments are analyzed for making a prediction, for example, when the body composition of the respective segments reaches a clinically significant target. An alert indication of the prediction may be generated and provided, for example, patient is predicted to reach target in the next 15 minutes. The prediction may be computed, for example, using a trend analysis (e.g., least square fit of a trend line to predict when the trend line will cross the threshold) and/or feeding the data into a machine learning model trained on data and an indication of a result, for example, a neural network.

Exemplary clinically significant targets include dehydration, and fluid overload.

Impedance values may be analyzed for computing the following exemplary health parameters:
ECW—extra cellular water which form the main conduction body at low frequencies.
ICW—Intra cellular water conducting at high frequency.
TBW—Total body water, indication of the body hydration status.
FFM—Fat free mass.
% body fat. Indication of obesity status of the patient.

Other parameters such as lungs water content may be calculated as part of the general patient status.

Reference is now made to FIG. 14, which includes some exemplary BIS equations, in accordance with some embodiments of the present invention.

Reference is now made to FIG. 15, which includes some exemplary equations for computing exemplary health parameters, in accordance with some embodiments of the present invention. The exemplary parameters may be computed for each of the monitored body segments.

At 216, the data and/or analyzed data is provided. The data and/or analyzed data may be presented on a display, for example, within a graphical user interface (GUI), stored in a memory (such as in the electronic health record of the patient, and/or locally on the computing device), and/or provided to another process for further processing (e.g., locally executed and/or executed on a remote server and/or cloud).

Optionally, the body composition for the respective body segments is presented within a GUI. The GUI may be dynamically updated in real time, as new impedance values are obtained and/or analyzed, for example, as described with reference to 220.

Optionally, the body composition of the respective body segments are presented (e.g., within the GUI) corresponding to a body map that depicts locations of the respective body segments.

Alternatively or additionally, the estimated amount of body composition of the respective segments are presented (e.g., within the GUI) as an indication along a range of different body compositions, for example, optionally color coded. For example, blue for body segments having a high water level and other color such as red for dehydrated body segments.

Optionally, a 3D map is computed and optionally presented using impedance measurements obtained at multiple different frequencies for each body segment. The 3D map may be presented using a linear gradient measurement based on the different frequencies.

Optionally, a trend line is computed and presented within the GUI. A target body composition may be presented with respect to the trend line. The visual presentation may help the user visualize when the body composition is predicted to reach the target according to the trend line.

Figure 16:
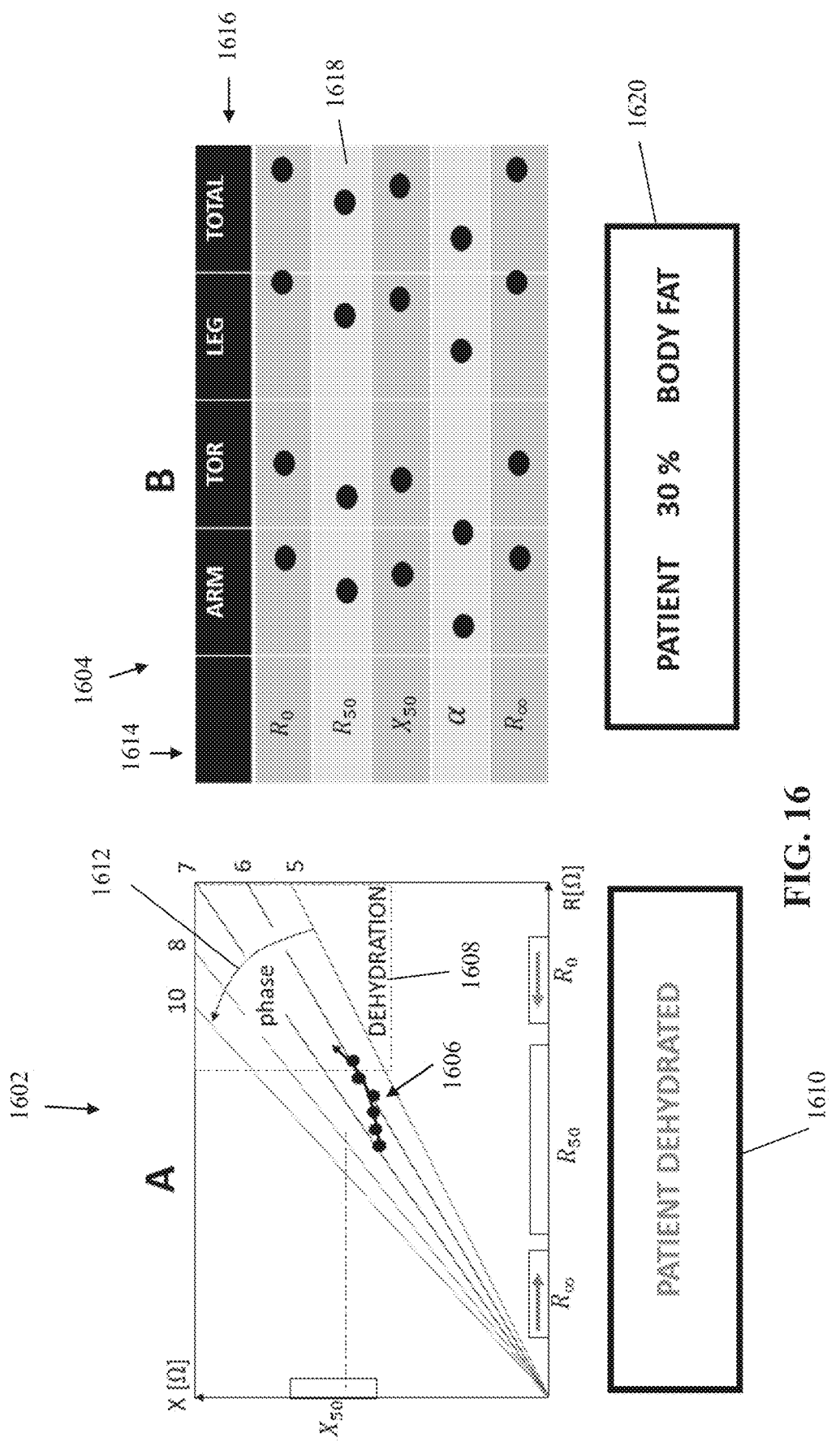
FIG. 16 is a schematic depicting exemplary presentations based on analyzed impedance measurements of body segments, in accordance with some embodiments of the present invention.

Reference is now made to FIG. 16, which is a schematic depicting exemplary presentations 1602 1604 based on analyzed impedance measurements of body segments, in accordance with some embodiments of the present invention. Presentations 1602 1604 may be presented, for example, within a GUI on a display of a client terminal, as described herein.

Presentation 1602 is a graph computed based on the Cole-Cole complex plan approach, where the measured impedance is mapped on an R-X complex plane. In the presented example of presentation 1602, the 50 kHz impedance (which may be considered a cardinal parameter) is mapped and a trend extrapolation 1606 is computed and presented. Portions of the R-X plane corresponding to clinically significant states (e.g., pathological states) may be defined. For example, region 1608 located in the upper right section of the R-X plane denotes dehydration. An alert 1610 denoting that the patient is dehydrated may be presented, for example, when the impedance measurements are located within dehydration region 1608 and/or when the trend indicates that the patient is not yet dehydrated but predicted to become dehydrated at a future time. An indication of a phase angle 1612 may be computed and presented. The phase angle and/or amplitude may be an important clinical factor, for example Piccoli suggested that the normal parameter value should be captive inside an ellipse and departure from the ellipse may be considered pathological.

Presentation 1604 is a table summarizing values of some clinical parameters (in a column 1614) for different body segments (in a row 1616), such as arm (e.g., left and/or right), torso, leg (e.g., left and/or right), and total (i.e., whole body). Each cell (e.g., 1618) in the table presents an indication of the corresponding clinical parameter for the corresponding body segment, for example, as a dot within a bar range. Other indications may be used, for example, numerical values, color coding, and category indications. One or more important parameters may be presented in a box 1620, for example, parameters selected by the user, parameters which are predefined as important, and/or parameters having abnormal clinically significant values.

Figure 17:
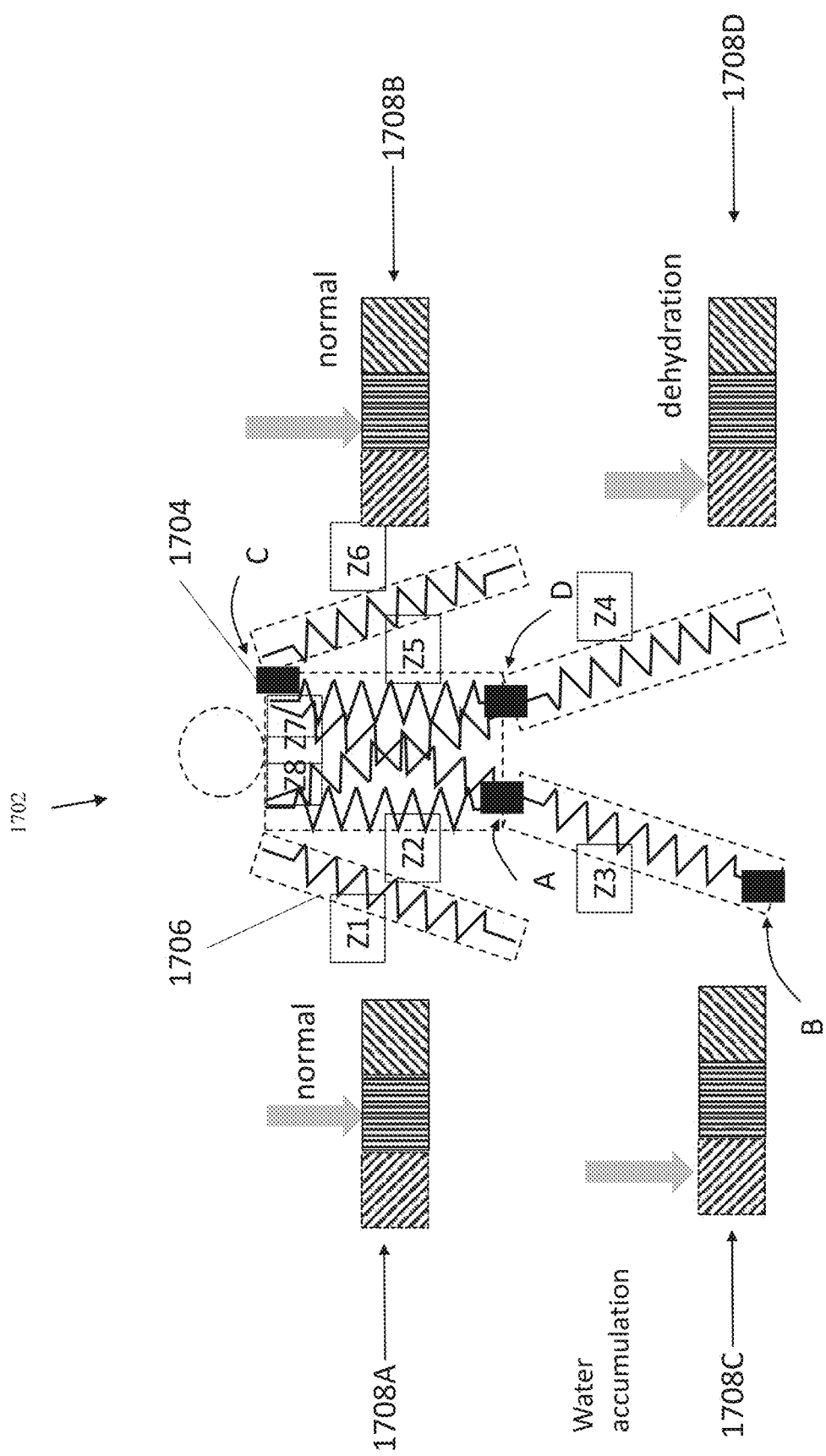
FIG. 17 is a schematic of an exemplary presentation of impedance data for multiple body segments, in accordance with some embodiments of the present invention.

Reference is now made to FIG. 17, which is a schematic of an exemplary presentation of impedance data for multiple body segments, in accordance with some embodiments of the present invention. The presentation may be presented on a display as a GUI, as described herein. The presentation may include a body map 1702, such as a schematic/image of a body of a patient. Monitored body segments may be presented with respect to body map 1702, for example, marked on body map 1702 and/or as an overlay on body map 1702, for example, as zigzag lines 1706. As shown, eight body segments are being monitored, denoted Z1, Z2, Z3, Z4, Z5, Z6, Z7, and Z8. Location of contact components (including electrodes) may be with respect to body map 1702, for example, marked on body map 1702 and/or as an overlay on body map 1702, for example, as a dark box 1704. The body segments right wrist-right shoulder Z1, right shoulder-right hip Z2, right hip-right ankle Z3, left ankle-left hip Z4, left hip-left shoulder Z5, left shoulder-left wrist Z6, left shoulder-right hip Z7, right shoulder-left hip Z8, may be monitored using 8 contact components (e.g., located on the left wrist, right wrist, left shoulder, right shoulder, left hip, right hip, left ankle, and right ankle, or in proximity to the stated locations). An indication of the amount of one or more monitored clinical parameter (computed based on an analysis of the impedance values, as described herein) may be presented for one or more body segments, for example, for each segment, for user selected segments, and/or for segments having abnormal values. The indication may be, for example, presented as an arrow with respect to a range, optionally color coded, denoting normal and abnormal values. For example, as shown, result icon 1708A denotes a normal value of fluid for body segment Z1 (e.g., arrow pointing to green colored zone of the values bar), result icon 1708B denotes a normal value of fluid for body segment Z6 (e.g., arrow pointing to green colored zone of the values bar), result icon 1708C denotes a high water accumulation amount for body segment Z3 (e.g., arrow pointing to blue colored zone of the values bar), and result icon 1708D denotes a dehydration state for body segment Z4 (e.g., arrow pointing to red colored zone of the values bar).

At 218, the patient may be diagnosed and/or treated and/or treatment may be planned according to the presented data, for example, according to the estimated body composition, for example, medications may be prescribed, fluids may be administered, imaging may be performed (e.g., chest xray, CT, MRI, such as when lung fluid is detected), a catheter may be inserted, tubes may be removed, surgical procedures may be performed, and/or nothing is done at the moment.

The diagnosis and/or treatment and/or treatment recommendation may be manually determined and/or automatically determined by code, for example, by a trained machine learning model trained on impedance values and corresponding actions taken by expert physicians.

The analysis and/or diagnosis and/or treatment recommendation may be performed remotely, for example by code residing in a cloud and/or server, in response to locally collected impedance data. The central processing of the data enables using data collected from different patients at different medical sites, increasing diversity of the data (e.g., different patient demographics, different clinical protocols followed, different levels of physician training, different available treatments).

At 220, one or more features described with reference to 206-218 are iterated, for example, for dynamic updating of the GUI, alerts, predictions, and/or indication of diagnosis.

Figure 19:
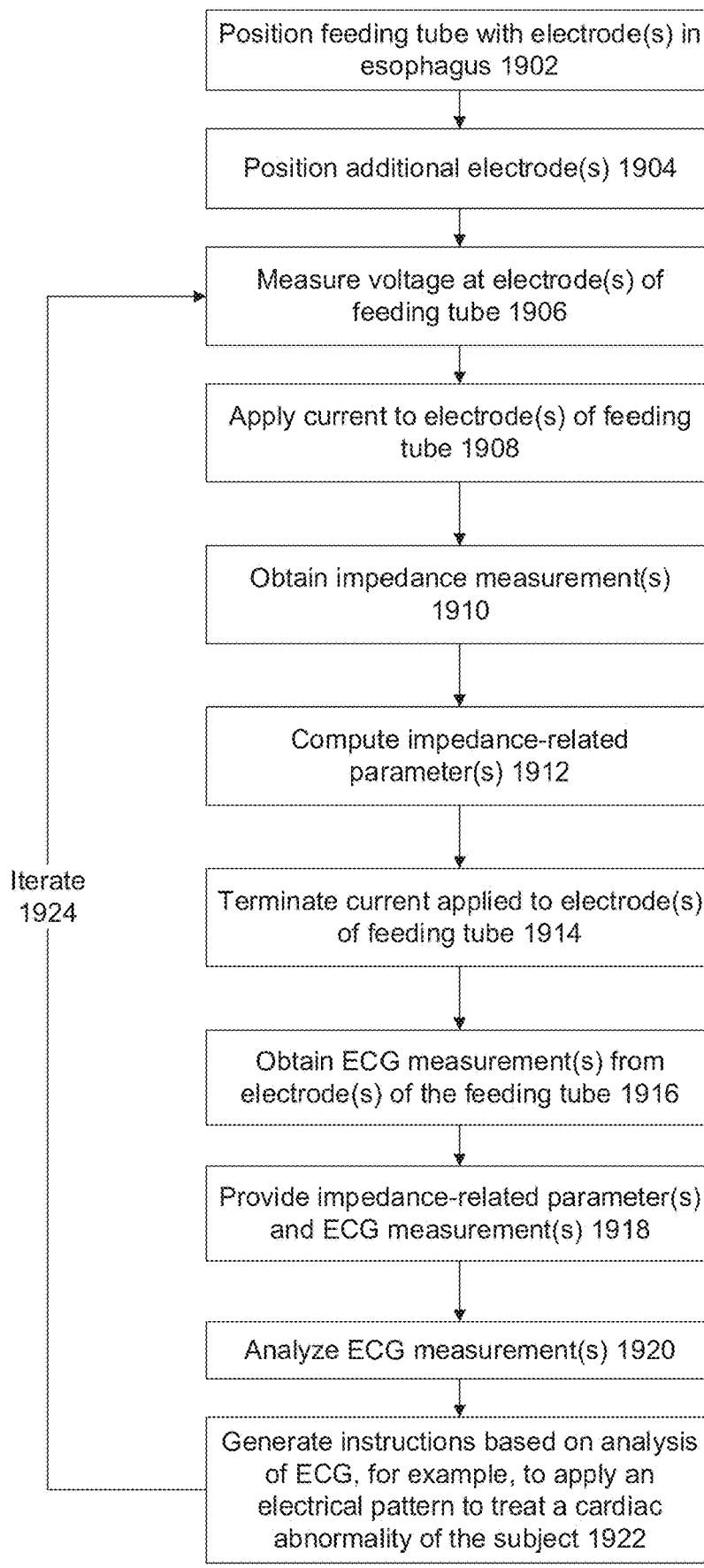
FIG. 19 is a flowchart of an exemplary process of monitoring a heart of a subject using electrocardiogram (ECG) measurements and/or monitoring impedance-related parameters and/or treating the subject based on the ECG measurements and/or the impedance-related parameters, where the ECG and impedance measurements are obtained from electrodes on a feeding tube positioned in the esophagus, in accordance with some embodiments of the present invention.

Reference is now made to FIG. 19, which is a flowchart of an exemplary process of monitoring a heart of a subject using electrocardiogram (ECG) measurements and/or monitoring impedance-related parameters and/or treating the subject based on the ECG measurements and/or the impedance-related parameters, where the ECG and impedance measurements are obtained from electrodes on a feeding tube positioned in the esophagus, in accordance with some embodiments of the present invention. The features of the methods described with reference to FIG. 19 may be implemented by components of system 100 described with reference to FIG. 1, and/or features of implementations described with reference to FIGS. 2-18. For example, by a controller implemented as computing device 104 that includes memory 106 storing code 106A that when executed by processor(s) 102, causes processor(s) 102 to execute features of the method described with reference to FIG. 19.

At 1902, the feeding tube is inserted into, and/or located at, a distal end of an esophagus of the subject. The feeding tube is positioned in the esophagus for enteral feeding of the subject.

One or more electrodes are located on the distal and of the feeding tube. When the tube is in the esophagus, in use for feeding, the electrode(s) are located at the distal end of the esophagus.

There may be multiple spaced apart electrodes on the feeding tube.

The feeding tube and/or electrodes may be as described herein.

At 1904, additional electrodes may be positioned on the body of the patient. The additional electrodes may be extracorporeal electrodes located externally to the body of the subject, and contacting the body of the subject.

Optionally, the additional electrodes are standard ECG electrodes applied to the skin surface of the chest of the subject in a standard ECG measurement arrangement. Alternatively or additionally, the additional electrodes are contact components, used for measuring impedance, as described herein. The contact components described herein may be used to obtain ECG measurements at different locations on the body, as described herein.

One or more of the following features described with reference to 1906-1924 are performed while the feeding tube is in located in the esophagus and feeding material is delivered to the patient via the feeding tube. This allows continuous and/or real time monitoring and/or treatment of the heart of the subject (and/or other features as described herein) while the patient is being fed.

At 1906, voltage is measured at one or more electrodes of the feeding tube. Voltage may be measured at one or more other electrodes, such as the extracorporeal electrodes, contact components, standard ECG electrodes, and the like.

When voltage is measured at the electrodes, no current is being administered via the electrodes (e.g., zero input current, or near zero). When no external current is present, the potential measured by the electrode(s) on the feeding tube in contact with the inner tissue of the esophagus is an indication of internal potential source originating from inside the observed tissue (excluding noise), which includes electrical signals generated by the heart.

Optionally, at least one electrode on the feeding tube is continuously in contact with inner tissue of the esophagus. The electrode(s) may be located on the feeding tube at a location corresponding to the lower esophageal sphincter (LES) (e.g., when the feeding tube is correctly positioned) so that the electrode is in continuous contact with the LES. In another example, one or more electrodes may be located on a balloon (and/or other expandable element) located on the feeding tube. The balloon may be expanded to contact the electrode(s) with the inner tissue of the esophagus.

Optionally, one or more electrodes on the feeding tube are not in contact with the inner tissue of the esophagus. For example, located along the length of the feeding tube above the LES, where the diameter of the feeding tube is significantly smaller than the diameter of the esophagus. Such electrodes may be used for monitoring reflux within the esophagus by measuring impedance.

Optionally, voltage is measured continuously, while one or more features described with reference to 1906-1914 are iterated. Alternatively, voltage is measured at spaced apart time intervals, and/or at certain time intervals, for obtaining ECG measurements and/or impedance measurements. ECG sample times may be defined, for example, at preselected time intervals, for example, about every 0.5 seconds, or 1 second, or 5 seconds, or 10 seconds, or 30 seconds, or 1 minute, or other time intervals. ECG may be sampled over a time interval sufficiently long to include one or more cardiac cycles, for example, at least about 1 second, or 5 seconds, or 10 seconds, or 30 seconds, or 1-30 seconds, or 5-20 seconds, or other time intervals.

At 1908, a current, optionally, an alternating current, is applied between one or more electrodes of the feeding tube and one or more other electrodes. The applied current establishes a current channel between the electrode(s) of the feeding tube and the other electrode(s). The alternating current may be applied at a selected frequency. Multiple AC currents may be applied, each at a respective frequency, for example, simultaneously and/or sequentially.

Optionally, the current is applied at the same electrode(s) where the voltage is being measured.

Optionally, the other electrode(s) may be other electrodes on the feeding tube, i.e., so that the current channel is established between a pair (or more) of electrode on the feeding tube. Alternatively or additionally, the other electrode(s) may be the extracorporeal electrodes and/or electrodes of the contact components.

Optionally, a non-cardiac current channel is established that avoids and/or reduces the amount of current flowing through the heart of the subject, for example, as described with reference to U.S. Application Publication No. 2019-0313970, by the same inventors of the present application.

At 1910, one or more impedance measurements are obtained from the electrode(s) of the feeding tube and/or from the other electrode(s). The impedance measurements are computed based on the applied current and the measured voltage.

At 1912, one or more impedance-related parameter may be computed based on the impedance measurements. Exemplary impedance related-parameters include:

An indication of location of the tube within the esophagus, for example, relative to the lower esophageal sphincter (LES). For example, to detect when the tube moves out of the correct position. Additional details of exemplary systems and/or methods for monitoring the position of a tube based on impedance measurements computed based on electrode(s) located on a tube positioned within the esophagus may be found with reference to U.S. Pat. No. 9,713,579, by the same inventors of the present application.

An estimate of a level of fluid within the digestive system. The enteral feeding (e.g., rate, mixture, amount of water, amount of protein) may be automatically adjusted according to the estimated fluid level, for example, to prevent reflux. Additional details of exemplary systems and/or methods for estimating fluid levels based on impedance measurements computed based on electrode(s) located on a tube positioned within the esophagus may be found with reference to International Patent Application No. IL2015/051156, by the same inventors of the present application.

An indication of body composition of a body segment located between the electrodes via which the current channel is established, for example, lung fluid, and/or other body composition indications as described herein.

An indication of reflux, i.e., detecting a gastric reflux event. For example, to stop enteral feeding. Additional details of exemplary systems and/or methods for detecting reflux event based on impedance measurements computed based on electrode(s) located on a tube positioned within the esophagus may be found with reference to International Patent Application No. IL2017/050634, by the same inventors of the present application.

An indication of breathing motion and/or motion of the diaphragm of the subject, optionally when the subject is being mechanically ventilated by a mechanical ventilator.

Estimate functionality of lung(s) according to a correlation between impedance values and lung function, and/or a correlation between lung fluid and lung function, for example, as described with reference to U.S. Application Publication No. 2019-0313970, by the same inventors of the present application. As lung fluid increases, the functionality of the lungs decreases. Functionality of the lungs may be for example, in terms of oxygen and carbon dioxide exchange, and/or air volume capacity of the lungs. Oxygen and carbon dioxide exchange is decreased due to the amount of tissue available to perform the exchange, since fluid filled tissue (i.e., pulmonary edema) cannot perform such exchange. Alternatively or additionally, the lung may be compressed from external fluid (e.g. pulmonary effusion) which reduces the volume of air capacity of the lung, reducing lung efficiency. The estimate of lung fluid (e.g., amount of fluid, change relative to a baseline) may be correlated to lung function, for example, according to a graph and/or function, which may be empirically measured and/or computed based on mathematical models. The estimated lung function may be computed as a change relative an initial baseline (e.g., 100%). For example, a certain increase in lung fluid may correspond to a 10% decrease in lung function. In another example, a 15% decrease in impedance may correspond to a 5% decrease in lung function.

At 1914, the application of the current (e.g., the alternating current), is terminated.

At 1916, an ECG measurement is obtained based on the voltage measured at least at one or more electrode(s) of the feeding tube. The ECG measurements is obtained while no current is being applied to the electrode(s) of the feeding tube.

Optionally, the ECG measurement is obtained from the electrode(s) contacting the inner surface of the esophagus, for example, the electrode(s) positioned on the feeding tube for contacting the LES and/or electrode(s) positioned on expandable elements (e.g., balloon) on the feeding tube when the expandable elements are expanded.

Optionally, multiple ECG measurements are obtained. ECG measurements may be obtained from each one of multiple spaced apart electrodes located on the distal end portion of the feeding tube. Each respective ECG measurement obtained at a respective electrode of the feeding tube denotes a different orientation relative to the heart of the subject. For example, one or more electrode(s) may be located on the feeding tube, so that when the feeding tube is in a predefined location (e.g., relative to the LES), the electrode(s) is in closest proximity to the sinoatrial node. Other electrodes may be positioned relatively higher and/or lower to capture ECG signals in proximity to other locations, for example, tricuspid valve right atrium, right ventricle, septum, mitral valve, left atrium, left ventricle, and/or other portions of the conduction system of the heart.

ECG measurements may be obtained after voltage(s) measured when no current is being applied undergo signal processing, for example, electronic filtering for removal of noise and/or unwanted electrical interactions. Filters may be tuned for detecting ECG, for example, matched filters tuned for ECG type wave forms, time domain moving window correlation for emphasizing the true ECG wave form while suppressing other spurious sources and/or noise. Since the ECG signals are of low frequency type (vis a vis capability of electronic circuits), sophisticated digital matched filtering may be applied.

At 1918, the measured impedance-related parameter and/or the ECG measurement may be provided, for example, presented on a display, stored in a memory, forwarded to a remote computing device (e.g., server, mobile device, smartphone), and/or provided to another process for further processing, for example, for analysis as described herein.

At 1920, the ECG measurements may be analyzed to determine an indication of cardiac abnormality, for example, arterial and/or ventricle pacing problems, cardiac arrest, and arrhythmias. The analysis may be automatically performed (e.g., by the controller and/or other computing device) and/or manually performed by a user (e.g., based on the presentation of the ECG on a display). The automatic analysis may be performed, for example, based on a set of rules, a trained classifier trained on a training dataset of ECG samples and labelled with a ground truth cardiac abnormality, and/or based on the T and/or QST portions.

Optionally, each one of multiple ECG measurements obtained from respective electrodes on the feeding tube may be analyzed individually. Alternatively, the multiple ECG measurements obtained from respective electrodes on the feeding tube may be analyzed as a combination, for example, as a group, to obtain an overlap state of the heart based on the ECGs obtained at different views.

The analysis of the ECG measurements obtained from electrode(s) on the feeding tube may include and/or be in combination with ECG measurements obtained from standard ECG electrodes applied to the chest of the subject.

Optionally, the ECG measurements are analyzed in combination with one or more impedance-related parameters. Optionally, The ECG measurements are analyzed with the impedance-related parameters indicative of body composition, for example, indicative of lung fluid. Alternatively or additionally, the ECG measurements are analyzed with the impedance-related parameters indicative of breathing and/or diaphragm motion, for example, indicative of the patient's breathing pattern. Alternatively or additionally, the ECG measurements are analyzed with the impedance-related parameters indicative of reflux, for example, to distinguish chest pain as being due to a cardiac condition (e.g., heart attack) versus reflux.

Optionally, the analysis of the ECG measurements, optionally in combination with one or more impedance-related parameters, is performed to determine likelihood of an abnormal cardiac condition. For example, tachycardia and/or conduction problems in the heart.

The analysis of the ECG measurements may be performed, for example, based on a set of rules, based on a mapping function, and/or based on a machine learning (ML) model such as a statistical classifier (e.g., neural network, regression function, support vector machine, and the like) trained on a training dataset of records of sample subjects that include ECG measurements obtained from electrodes on a feeding tube positioned in the esophagus of the respective subject and corresponding ground truth cardiac conditions (e.g., determined by qualified physicians).

Optionally, the analysis is performed based on a combination of ECG measurements and body composition (i.e., impedance-related parameter(s)), for example, indicating amount of lung fluid in lung(s) of the subject Likelihood of the cardiac abnormality may be determined based on the combination of ECG and body composition. For example, the ECG may indicate a certain cardiac abnormality (e.g., tachycardia) which may or may not be a clinical urgency. When the body composition parameters indicate a rising amount of fluid in the lung(s), the combined analysis may indicate that the tachycardia is causing improper pumping by the heart, leading to the fluid buildup in the lungs. The tachycardia may be treated accordingly, for example, by a suitable electrical pattern.

Optionally, the impedance-related parameter of a certain electrode(s) of the feeding tube is analyzed to identify whether the certain electrode(s) is in contact with the LES. The contact between the certain electrode and the LES denotes that the feeding tube is in a target location. When the feeding tube is in the target location, the electrodes on the feeding tube are located at their respective target positions for obtaining ECG measurements at target views of the heart. The ECG measurements obtained at the target views may increase accuracy of the analysis for determining likelihood of cardiac abnormality.

At 1922, instructions may be generated based on the analysis of the ECG and/or impedance-related parameters, for example, for execution by the controller and/or other computing devices and/or other controllers. The instructions may be for treatment of the subject.

Optionally, the instructions are for applying an electrical pattern for treatment of the abnormal cardiac condition detected based on the analysis of ECG (and/or other impedance-related parameters). The electrical pattern may be selected according to the determined abnormal cardiac condition.

The electrical pattern may be applied using the electrode(s) located on the feeding tube, optionally from the same electrode(s) on the feeding tube from which the ECG measurement is sensed. The electrical pattern may be applied by a single electrode, or multiple electrodes, for example, when a respective ECG is obtained from a respective electrode. For example, for the case of multiple electrodes, the electrical pattern for each electrode may be determined (e.g., computed) in order to obtain a synergistic effect for treatment of the heart, and/or in order to reduce the energy of the current applied to the heart at one location by delivering lower energy current from multiple different locations.

Optionally, electrode(s) are selected for applying the electrical pattern. Certain selected electrodes may be activated, for example, by expanding the expandable element (e.g., inflating a balloon on which the electrode(s) is located) for contacting the inner surface of the esophagus. Such electrode(s) may be selected for applying the electrical pattern at selected regions, for example, higher up along the esophagus (from the LES) to target the atria and/or lower down the esophagus (closer to the LES) to target the ventricle(s). The electrical pattern may be applied when the electrode is in contact with the inner surface of the esophagus. The expandable element may be contracted (e.g., the balloon is deflated) after the electrical treatment.

Exemplary electrical patterns include: (i) Defibrillation electrical pattern, for example, for treating the cardiac abnormality of ventricular fibrillation (VF) and/or ventricular tachycardia (VT). (ii) Cardiac pacing electrical pattern, for example, for treating the cardiac abnormality of abnormal heart rate and/or block in electrical conduction in the heart. (iii) Cardioversion electrical pattern, for example, for treating the cardiac abnormality of cardiac arrhythmia convertible to normal sinus rhythm.

Optionally, the electrical pattern applied via the electrode(s) of the feeding tube has significantly less power (e.g., lower amplitude pulse) in comparison to an electrical pattern that would otherwise be applied in a standard approach (e.g., using a standard defibrillator and/or electrodes for cardioversion) via extracorporeal electrodes to a skin surface of a chest of the subject. For example, the electrical pattern applied via the electrode(s) of the feeding tube has a power of less than about 40, or 50, or 60 Joules, in comparison to standard approaches that apply the electrical pattern via extracorporeal electrodes to the chest, in the range of about 100 to 500 Joules. The lower energy electrical pattern applied by the electrodes of the feeding tube may obtain the same treatment effect as a higher energy electrical pattern applied by extracorporeal electrodes applied to the chest in a standard approach.

Alternatively or additionally, instructions are generated according to the ECG measurement obtained from the electrode(s) of the feeding tube and/or the impedance-related parameters, for adapting feeding and/or medication of the subject by a feeding controller that delivers feeding materials via the feeding tube. For example, the type of feeding material, the rate of feeding material, the composition of the feeding material, supplements to the feeding material (e.g., protein), and/or delivered water, may be adjusted according to the ECG measurements and/or impedance-related parameters. For example, subjects with certain cardiac abnormalities may benefit from certain nutritional supplements, for example, extra potassium and/or magnesium.

Optionally, the instructions are for halting the feeding of the subject, for example, feeding is halted when an abnormal cardiac condition is detected. The subject may be treated for the cardiac condition using electrical patterns applied via the electrode(s) of the feeding tube, in response to the halting of the feeding. The halting of the feeding during application of the electrical pattern may help reduce risk of vomiting and/or reflux, which may lead to aspiration pneumonia and/or asphyxiation.

Optionally, the instructions are for generating an indication, for example, a presentation on a display, indicating a differentiation between gastric reflux and a cardiac abnormality. For example, for a patient experiencing chest pain, the pain may be due to reflux, or may be due to a heart attack. The differentiation between gastric reflux and the cardiac abnormality may be performed by analyzing the impedance-related parameters computed from impedance measurements of the electrode(s) of the feeding tube to detect whether gastric reflux is present in the esophagus, and/or by analyzing the ECG measurements obtained from the electrode(s) of the feeding tube to detect whether the cardiac abnormality is present.

Alternatively or additionally, the instructions are for generating for execution by a mechanical ventilator that mechanically ventilates the patient, for adjustment of a mechanical ventilation pattern applied to the patient for treating a respiratory abnormality. The respiratory abnormality may be detected based on an analysis of a combination of the ECG measurement and breathing parameter(s) (i.e., impedance-related parameters) to determine likelihood of a combined cardiac abnormality and/or respiratory abnormality. For example, tachycardia leading to insufficient blood pumping may lead to fluid buildup in the lungs, which may lead to the patient having difficulty breathing. The patient may be provided with additional oxygen by the mechanical ventilator and/or the tachycardia may be treated with suitable electrical patterns. Examples of processes for adjusting the mechanical ventilator based on impedance measurements obtained from electrode(s) on a feeding tube are described, for example, with reference to U.S. Publication No. 2019-0083725, by the same inventors as the present application.

The generated instructions may be executed by the respective controller and/or computing device, for example, for treatment of the abnormal cardiac condition of the subject by electrical patterns.

At 1924, one or more of 1906-1924 are iterated, for continuously (and/or sequential time interval) monitoring for cardiac abnormalities of the heart of the subject (i.e., via ECG measurements obtained from electrode(s) on the feeding tube) and/or treatment of the cardiac abnormality (i.e., via the electrode(s) on the feeding tube) and/or monitoring impedance-related parameters and/or generating suitable instructions, while the patient is being fed via the feeding tube, as described herein.

The iteration(s) may be performed after the electrical pattern is applied, in order to monitoring the ECG to determine whether the treatment is effective or not. When the treatment is non-effective, the same treatment may be re-applied, the previous treatment may be adjusted (e.g., increase power), and/or a new treatment may be selected (e.g., new electrical pattern).

The monitoring of the contact between the certain electrode(s) of the feeding tube and the LES may be iteratively performed for confirming continuous contact between certain electrode(s) and the LES during the measurements of the ECG.

Figure 20:
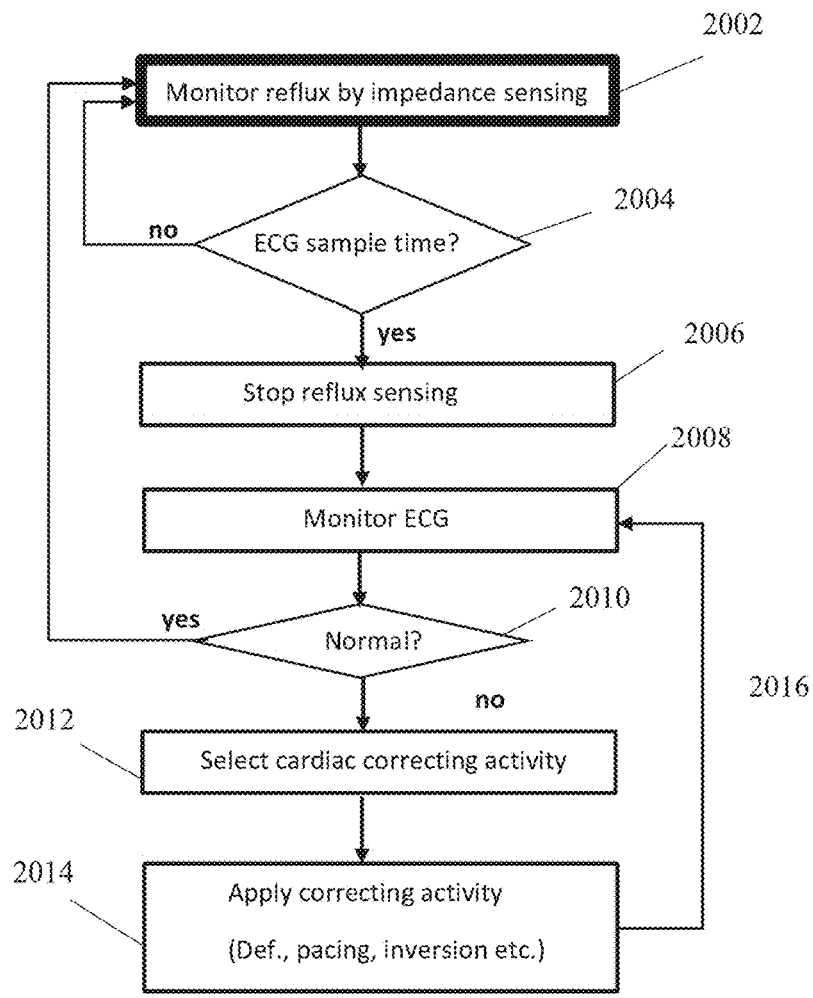
FIG. 20 is a flowchart of an exemplary process of monitoring a heart of a subject using ECG measurements and/or monitoring for reflux using electrodes located on a feeding tube positioned in the esophagus, in accordance with some embodiments of the present invention.

Reference is now made to FIG. 20, which is a flowchart of an exemplary process of monitoring a heart of a subject using electrocardiogram (ECG) measurements and/or monitoring for reflux using electrodes located on a feeding tube positioned in the esophagus, in accordance with some embodiments of the present invention. Features of the method described with reference to FIG. 20 may correspond to, be combined with, and/or be substituted with features described with reference to FIG. 19. The features of the methods described with reference to FIG. 20 may be implemented by components of system 100 described with reference to FIG. 1, and/or features of implementations described with reference to FIGS. 2-19. For example, by a controller implemented as computing device 104 that includes memory 106 storing code 106A that when executed by processor(s) 102, causes processor(s) 102 to execute features of the method described with reference to FIG. 20.

At 2002, reflux is monitored by impedance sensing at the electrode(s) located on the feeding tube located in the esophagus, as described herein. A current, optionally an alternating current at a selected frequency, is applied to the electrode(s) on the feeding tube. Voltage is sensed at the electrode(s) on the feeding tube. Impedance is computed from the applied current and sensed voltage.

At 2004, an evaluation may be performed to determine whether ECG is to be measured, by determining whether it is currently an ECG sample time.

When it is not currently ECG sample time, 2002 is iterated for continuously and/or repeatedly monitoring for reflux. When it is currently ECG sample time, the process continues to 2006.

At 2006, reflux sensing is stopped, by stopping the injection of current into the electrode(s) on the feeding tube.

At 2008, ECG is monitored at the electrode(s) on the feeding tube, by sensing voltage at the electrode(s) on the feeding tube when no current is being injected into the electrode(s) on the feeding tube.

At 2010, the ECG measurements may be analyzed to determine whether a cardiac abnormality is present. The analysis may be performed, for example, automatically (e.g., based on a set of rules, a trained classifier, and/or other approaches), and/or manually (e.g., presenting the ECG on a display, and a user enters an indication of whether the cardiac abnormality is present).

When according to the analysis, the ECG measurements are determined to be indicative of normal and/or presence of a cardiac abnormality being unlikely, 2002-2010 are iterated. Alternatively, when according to the analysis, the ECG measurements are determined to be indicative of likelihood of the cardiac abnormality being present, the process continues to 2012.

At 2012, a suitable cardiac correcting activity is selected according to the ECG measurements, for example, as described herein. The suitable cardiac correcting activity may be a certain electrical pattern, for example, defibrillation, pacing, and inversion.

At 2014, the selected cardiac correcting activity, optionally the selected electrical pattern, is applied to the subject using the electrode(s) on the feeding tube for treating the cardiac abnormalitiy. The same electrode(s) used to measure ECG may be used for applying the electrical pattern. Alternatively, different electrode(s) on the feeding tube may be used for applying the electrical pattern and measuring ECG. Alternatively, some electrodes may be used for both measuring ECG and applying the electrical pattern and other electrodes are used only for ECG and others only for applying the electrical patterns.

At 2016, the process iterates from 2008 to monitor ECG to determine whether the applied electrical activity successfully treated the subject (2010) or whether additional treatment is to be provided (2012-2014).

Figure 21:
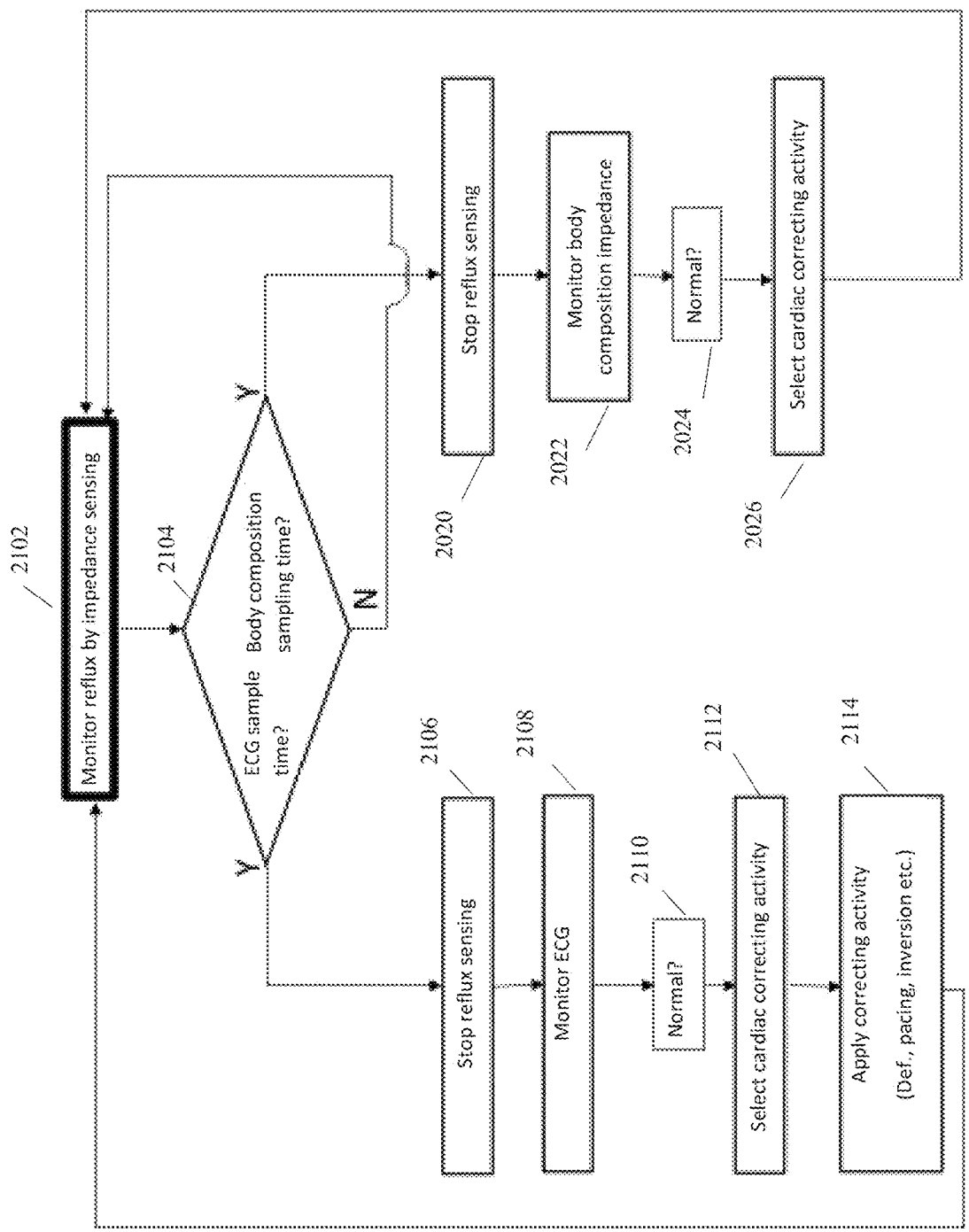
FIG. 21 is a flowchart of an exemplary process of monitoring a heart of a subject using ECG measurements and/or monitoring for reflux and/or measuring body composition using electrodes located on a feeding tube positioned in the esophagus, in accordance with some embodiments of the present invention.

Reference is now made to FIG. 21, which is a flowchart of an exemplary process of monitoring a heart of a subject using electrocardiogram (ECG) measurements and/or monitoring for reflux and/or measuring body composition (e.g., lung fluid) using electrodes located on a feeding tube positioned in the esophagus, in accordance with some embodiments of the present invention. Features of the method described with reference to FIG. 21 may correspond to, be combined with, and/or be substituted with features described with reference to FIG. 19 and/or FIG. 20. The features of the methods described with reference to FIG. 21 may be implemented by components of system 100 described with reference to FIG. 1, and/or features of implementations described with reference to FIGS. 2-20. For example, by a controller implemented as computing device 104 that includes memory 106 storing code 106A that when executed by processor(s) 102, causes processor(s) 102 to execute features of the method described with reference to FIG. 21.

At 2102, reflux is monitored by impedance sensing at the electrode(s) located on the feeding tube located in the esophagus, for example, as described herein and/or with reference to 2002 of FIG. 20.

At 2104, an evaluation may be performed to determine whether ECG is to be measured, for example, as described with reference to 2004 of FIG. 20 (e.g., by determining whether it is currently an ECG sample time) or whether body composition sampling (e.g., lung fluid) is to be estimated (e.g., by determining whether it is currently a body composition sampling time).

When it is not currently ECG sample time, 2102 is iterated for continuously and/or repeatedly monitoring for reflux. When it is currently ECG sample time, the process continues to 2106. Alternatively, when it is currently body composition sampling time, the process continues to 2020.

At 2106, reflux sensing is stopped by stopping the injection of current, for example, as described herein and/or with reference to 2006 of FIG. 20.

At 2108, ECG is monitored, for example, as described herein and/or with reference to 2008 of FIG. 20.

At 2110, the ECG is analyzed to determine whether the ECG denotes normal and/or likelihood of no cardiac abnormality, or whether the ECG denotes abnormal cardiac activity, for example, as described herein and/or with reference to 2010 of FIG. 20.

At 2112, cardiac correcting activity (e.g., electrical patterns) is selected, for example, as described herein and/or with reference to 2012 of FIG. 20.

At 2114, the selected cardiac correcting activity is applied, for example, as described herein and/or with reference to 2014 of FIG. 20.

The process then iterates from 2102.

Alternatively, at 2020, reflux sensing is stopped, for example, as described herein and/or with reference to 2006 of FIG. 20. It is noted that for body composition monitoring, the injection of current may be continued. Current may be adjusted, for example, a different frequency may be selected for the alternating current.

At 2022, body composition is monitored by computing impedance based on the selected frequency of the injected current and sensed voltage, as described herein. Body composition may be monitored for a body segment that includes the electrode(s) on the feeding tube, for example, the lungs and/or lobes of the lungs, for example, for measuring lung fluid therein, as described herein.

At 2024, the body composition may be analyzed to determine whether a cardiac abnormality is present. The body composition may be analyzed in combination with the ECG measurement, for example, as described herein. For example, a cardiac abnormality and an increase in lung fluid may denote a clinically significant condition that requires immediate treatment.

The analysis may be performed, for example, automatically (e.g., based on a set of rules, a trained classifier, and/or other approaches), and/or manually (e.g., presenting the ECG and/or body composition values on a display, and a user enters an indication of whether the cardiac abnormality is present).

When according to the analysis, the body composition measurements (and optionally in combination with ECG measurements) are determined to be indicative of likelihood of the cardiac abnormality being present, the process continues to 2026.

At 2026, a suitable cardiac correcting activity may be selected and applied, for example, as described with reference to 2112-2114.

The process then iterates from 2102.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant electrodes will be developed and the scope of the term electrode is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for measuring impedance for estimating body composition in a body segment of a patient, comprising:
   a plurality of contact circuitry, each contact circuity is an independent physical structure designed to be independently positioned at different locations of a body of the patient, each contact circuitry including three electrodes for contacting the body of the patient arranged along a long axis of the contact circuitry, each contact circuitry associated with a different unique address and assignment, wherein the plurality of contact circuitry are spaced apart and independently positionable at the different locations;
   a conductor, wherein the three electrodes of the plurality of contact circuitry are sequentially spaced apart along the conductor and electrically connected in series to the conductor; and
   a controller that transmits on the conductor, a signal indicative of the respective unique address and assignment of a first contact circuitry and a second contact circuity of a first pair of contact circuitry of the plurality of contact circuitry, the first contact circuity and the second contact circuity of the first pair located at opposite ends of the body segment, wherein the signal is transmitted to the plurality of contact circuitry serially connected and sequentially located along the conductor, the signal transmitted to other contact circuitry of the plurality of contact circuitry being different than the first pair of contact circuitry,
   the controller configured to operate a middle electrode of the three electrodes of the first contact circuity for transmission of current, and to operate an inner facing electrode of the three electrodes of the second contact circuitry of the first pair for voltage measurement, obtain the current and the voltage measurement for computing at least one impedance measurement indicative of the impedance of the body segment, and provide the at least one impedance measurement for estimation of the body composition of the body segment,
   wherein the controller iteratively selects a second pair of contact circuitry of the plurality of contact circuitry connected by the conductor, and collects a second impedance measurement by measuring impedance using the electrodes of the second pair of contact circuitry, the second impedance measurement indicative of an impedance of a second body segment located between the second pair of contact circuitry, and provides the second impedance measurement for estimation of a second body composition of the second body segment, including muscle mass and/or fat free mass of the second body segment,
   wherein a same contact circuitry is a member of the second pair of contact circuitry and of the first pair of contact circuitry.

2. The system of claim 1, wherein the body composition is selected from the group consisting of: fat content, water composition, edema, water content, electrolyte content, and pathological status.

3. The system of claim 1, wherein the conductor further comprises an instruction line for transmitting instructions for an operation mode of at least one of: the middle electrode of the three electrodes of the first contact circuitry and the inner facing electrode of the three electrodes of the second contact circuitry having the unique address, for defining operation as one of: a current source, a current sink or voltage sensor, the controller configured to issue the instructions.

4. The system of claim 1, wherein the plurality of contact circuitry and the conductor are integrated into a single flexible strip.

5. The system of claim 1, wherein the conductor connects between the controller and each one of the plurality of contact circuitry.

6. The system of claim 1, wherein each of the three electrodes of each contact circuitry has a respective unique address, and the controller selects a pair of electrodes of the first pair of contact circuitry by addressing each one of the pair of electrodes.

7. The system of claim 1, wherein at least one contact circuitry of the first pair of contact circuitry is positioned between the second pair of contact circuitry, and the first pair of contact circuitry and the second pair of contact circuitry are connected to the conductor.

8. The system of claim 7, wherein at least one contact circuitry of the first pair of contact circuitry is configured to ignore second instructions issued by the controller to the second pair of contact circuitry during the second impedance measurement performed for the second body segment located between the second pair of contact circuitry.

9. The system of claim 1, wherein the controller injects and receives the current using the middle electrode of the three electrodes of each contact circuitry of the first pair and second pair of contact circuitry, and the controller measures voltage using inner facing electrodes of the three electrodes of each contact circuitry of the first pair of contact circuitry and the second pair of contact circuitry.

10. The system of claim 1, wherein the at least one impedance measurement comprises a first impedance measurement, and wherein the controller iteratively switches between the first pair and second pair of contact circuitry to monitor the first impedance measurement over a time interval for the body segment and monitor the second impedance measurement over the time interval for the second body segment.

11. The system of claim 10, further comprising code for analyzing the first impedance measurement and the second impedance measurement to predict when at least one of the body composition of the body segment and the second body composition of the second body segment reach a target, and generating an alert indicative of the prediction.

12. The system of claim 1, further comprising an intra-body tube for insertion into a lumen of the body of the patient, the intra-body tube coupled to a first set of contact circuitry of the plurality of contact circuitry for contacting an inner surface of the body of the patient, wherein the conductor is connected to the first set of contact circuitry of the intra-body tube and to a second set of contact circuitry positioned exterior to the body of the patient, the first pair of contact circuitry including the first set of contact circuitry of the intra-body tube and one contact circuitry of the second set positioned exterior to the body of the patient.

13. The system of claim 1, wherein a space between any two of the plurality of contact circuitry is larger than a space between any two of the three electrodes of any one of the plurality of contact circuitry.

\* \* \* \* \*